United States Patent
Gynther et al.

(10) Patent No.: US 7,173,024 B2
(45) Date of Patent: Feb. 6, 2007

(54) COMPOUNDS HAVING PROLYL OLIGOPEPTIDASE INHIBITORY ACTIVITY, METHODS FOR THEIR PREPARATION AND THEIR USE

(75) Inventors: Jukka Gynther, Kuopio (FI); Pekka Männistö, Helsinki (FI); Erik Wallen, Kuopio (FI); Johannes Christiaans, Utrecht (NL); Markus Forsberg, Kuopio (FI); Antti Poso, Pieksämäki (FI); Jarkko Venäläinen, Kuopio (FI); Elina Jarho, Kuopio (FI)

(73) Assignee: Orion Corporation, Espoo (FI)

( * ) Notice: Subject to any disclaimer, the term of this patent is extended or adjusted under 35 U.S.C. 154(b) by 50 days.

(21) Appl. No.: 10/482,700

(22) PCT Filed: Jul. 4, 2002

(86) PCT No.: PCT/FI02/00607

§ 371 (c)(1),
(2), (4) Date: Jun. 8, 2004

(87) PCT Pub. No.: WO03/004468

PCT Pub. Date: Jan. 16, 2003

(65) Prior Publication Data

US 2005/0020677 A1 Jan. 27, 2005

(30) Foreign Application Priority Data

Jul. 4, 2001 (FI) .................................. 20011466

(51) Int. Cl.
*A61K 31/55* (2006.01)
*A61K 31/535* (2006.01)
*A61K 31/497* (2006.01)
*A61K 31/401* (2006.01)
*C07D 207/08* (2006.01)
*C07D 413/08* (2006.01)
*C07D 413/10* (2006.01)
*C07D 403/06* (2006.01)
*C07D 403/10* (2006.01)

(52) U.S. Cl. ......................... 514/217.08; 514/232.2; 514/254.01; 514/422; 514/423; 540/602; 544/82; 544/372; 548/524

(58) Field of Classification Search ............... None
See application file for complete search history.

(56) References Cited

U.S. PATENT DOCUMENTS 6,103,910 A * 8/2000 Hertel et al. ............... 548/523

6,121,311 A   9/2000 Matsubara et al.
6,512,001 B1 * 1/2003 Hertel et al. ............... 514/422

FOREIGN PATENT DOCUMENTS

| EP | 0 468 339 A2 | 1/1992 |
|---|---|---|
| EP | 0 915 088 A1 | 5/1999 |
| WO | WO 91/18891 | 12/1991 |

OTHER PUBLICATIONS

Kogiso, et al. "Dicarboxylic Oligopeptide Bolaamphiphiles: Proton-Triggered Self-Assembly of Microtubes with Loose Solid Surfaces" Langmuir, vol. 14, pp. 4978-4986 (1998).*
Fiona M. Anderson et al., "Synthesis of new homochiral bispyrrolidines as potential DNA cross-linking antitumour agents," Anti-Cancer Drug Design, vol. 15, 2000, pp. 119-126.
N. A. Grigoryan et al., "Synthesis and antistaphylococcal activity of dicarboxylic acid derivatives containing an amino acid fragment," Chemical Abstracts, vol. 117, Oct. 26, 1992.
L. Colombo et al., "Enantioselective Synthesis of Secondary Alcohols in the Presence of Chiral Ligands," Tetrahedron, vol. 38, No. 17, 1982, pp. 2725-2727.
Sherwin Wilk, "Minireview Prolyl Endopeptidase," Life Sciences, vol. 33, 1983, pp. 2149-2157.
Rhonda O'Leary et al., "Thyrotropin-Releasing Hormone," Journal of Neurochemistry, vol. 65, No. 3, 1995, pp. 953-963.
Tadashi Yoshimoto et al., "Specific Inhibitors for Prolyl Endopeptidase And Their Anti-Amnesic Effect," J. Pharmacobio-Dyn, vol. 10, 1987, pp. 730-735.
Neil W. Kowall et al., "An in vivo model for the neurodegenerative effects of β amyloid and protection by substance P," Proc. Natl. Acad. Sci. USA, vol. 88, 1991, pp. 7247-7251, Aug. 1991.

(Continued)

*Primary Examiner*—Joseph K. McKane
*Assistant Examiner*—Nyeemah Grazier
(74) *Attorney, Agent, or Firm*—Finnegan, Henderson, Farabow, Garrett & Dunner, LLP

(57) ABSTRACT

Compounds of the formula (I),

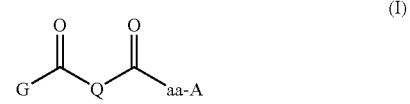

wherein the symbol aa means a residue of an α-amino acid. The invention is also directed to a method for the preparation of the compounds of formula (I), as well as their use as prolyl oligopeptide inhibitors, for example for the treatment of Alzheimer's disease.

12 Claims, No Drawings

OTHER PUBLICATIONS

Katsuo Toide et al., "JTP-4819: A Novel Prolyl Endopeptidase Inhibitor with Potential as a Cognitive Enhancer," J. Pharmacol. Exp. Ther., 1995, vol. 274, pp. 1370-1378.

Guillaume DeNanteuil et al., "Prolyl endopeptidase inhibitors: a new class of memory enhancing drugs," J. Drugs Fut., 1998, vol. 23, pp. 167-179.

Beilstein Data: Beilstein Registry No. 1805844, Beilstein Institut zur Foerderung der Chemischen Wissenschaften, copyright 1988-2005.

Beilstein Data: Beilstein Registry No. 8705350, Beilstein Institut zur Foerderung der Chemischen Wissenschaften, copyright 1988-2005.

Beilstein Data: Beilstein Registry No. 1803243, Beilstein Institut zur Foerderung der Chemischen Wissenschaften, copyright 1988-2005.

Beilstein Data: Beilstein Registry No. 6503093, Beilstein Institut zur Foerderung der Chemischen Wissenschaften, copyright 1988-2005.

Beilstein Data: Beilstein Registry No. 3484140, Beilstein Institut zur Foerderung der Chemischen Wissenschaften, copyright 1988-2005.

Beilstein Data: Beilstein Registry No. 2483846, Beilstein Institut zur Foerderung der Chemischen Wissenschaften, copyright 1988-2005.

Beilstein Data: Beilstein Registry No. 4023304, Beilstein Institut zur Foerderung der Chemischen Wissenschaften, copyright 1988-2005.

Beilstein Data: Beilstein Registry No. 7312852, Beilstein Institut zur Foerderung der Chemischen Wissenschaften, copyright 1988-2005.

Beilstein Data: Beilstein Registry No. 2404859, Beilstein Institut zur Foerderung der Chemischen Wissenschaften, copyright 1988-2005.

* cited by examiner

COMPOUNDS HAVING PROLYL OLIGOPEPTIDASE INHIBITORY ACTIVITY, METHODS FOR THEIR PREPARATION AND THEIR USE

This application is a U.S. national stage filing of PCT International Application No. PCT/FI02/00607, filed on Jul. 4, 2002, which claims the benefit of priority to Finnish patent application no. 20011466, filed on Jul. 4, 2001.

FIELD OF THE INVENTION

The present invention concerns compounds having prolyl oligopeptidase inhibitory activity, methods for their preparation and their use, especially in the form of a pharmaceutical preparation.

BACKGROUND OF THE INVENTION

Prolyl oligopeptidase (EC, 3.4.21.26), also known as prolyl endopeptidase, is the only serine protease that catalyses the hydrolysis of peptides at the C-terminal side of L-proline residues. It is widely distributed in mammals and can be purified from various organs, including the brain.

The enzyme plays an important role in the breakdown of proline-containing neuropeptides related to learning and memory functions (Wilk, S., *Life Sci.*, 33, 2149–2157 (1983); O'Leary, R. M., O'Connor, B., *J. Neurochem.*, 65, 953–963 (1995)). Compounds capable of inhibiting prolyl oligopeptidase are effective for preventing experimental amnesia induced by scopolamine in rats, inferring that prolyl oligopeptidase inhibitors have functions in the fixation of memory (Yoshimoto, T., Kado, K., Matsubara, F., Koryama, N., Kaneto, H., Tsuru, D., *J. Pharmacobio-Dyn.*, 10, 730–735 (1987)).

In recent years it has been found that β-amyloid protein shows neurotoxic action in in vitro and in vivo experiments and that it plays an important role in the onset of Alzheimer's disease. In view of the hypothesis that substance P can suppress neurotoxic action of β-amyloid protein (Kowall, N. W., Beal, M. F., Busciglio, J., Duffy, L. K., Yankner, B. A., *Proc. Natl. Acad. Sci. USA*, 88, 7247–7251 (1991)), it is speculated that prolyl oligopeptidase inhibitors that inhibit also metabolism of substance P can make an effective drug for the treatment of Alzheimer's disease.

SUMMARY OF THE INVENTION

The present invention relates to novel prolyl oligopeptidase inhibitors having the general formula:

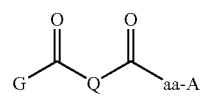

(I)

In the formula, the symbol Q means:
a covalent bond,
a straight or branched, substituted or unsubstituted alkylene chain having 1 to 10 carbon atoms,
a straight or branched, substituted or unsubstituted alkenylene chain having 2 to 10 carbon atoms,
a substituted or unsubstituted arylene group,
a substituted or unsubstituted cycloalkylene or a cycloalkenylene group with 3 to 10 carbon atoms,
a substituted or unsubstituted alkylene or alkenylene chain as defined above incorporating as a chain member a substituted or unsubstituted cycloalkylene, cycloalkenylene or an arylene group as defined above;

the symbol A means:
a straight or branched, substituted or unsubstituted alkyl chain having 1 to 10 carbon atoms,
a straight or branched, substituted or unsubstituted alkenyl chain having 2 to 10 carbon atoms,
a 3 to 7 membered saturated or unsaturated, substituted or unsubstituted carbocyclic ring,
a 3 to 7 membered saturated or unsaturated, substituted or unsubstituted heterocyclic ring,
a substituted or unsubstituted alkyl or alkenyl group as defined above incorporating as a group member a substituted or unsubstituted carbocyclic ring or a heterocyclic ring as defined above,
lower alkoxy, aryloxy, aryl lower alkoxy, amino, lower alkyl amino, aryl amino or aryl lower alkyl amino, wherein the alkyl, aryl or aralkyl subgroups can be substituted or unsubstituted;

the symbol G means-aa'-E, wherein E means:
a straight or branched, substituted or unsubstituted alkyl chain having 1 to 15 carbon atoms,
a straight or branched, substituted or unsubstituted alkenyl chain having 2 to 15 carbon atoms,
a 3 to 7 membered, saturated or unsaturated, substituted or unsubstituted carbocyclic ring,
a 3 to 7 membered saturated or unsaturated, substituted or unsubstituted, heterocyclic ring,
a substituted or unsubstituted alkyl or alkenyl group as defined above incorporating as a group member a substituted or unsubstituted carbocyclic ring or a heterocyclic ring as defined above,
hydroxy, lower alkoxy, aryloxy, aryl lower alkoxy, amino, lower alkyl amino, aryl amino or aryl lower alkyl amino, wherein the alkyl, aryl or aralkyl subgroups can be substituted or unsubstituted;

or the symbol G means E', wherein E'means:
a 3 to 7 membered saturated or unsaturated, substituted or unsubstituted, amino functionality containing heterocyclic ring,
amino, lower alkyl amino, aryl amino or aryl lower alkyl amino, wherein the alkyl, aryl or aralkyl subgroups can be substituted or unsubstituted;

the symbols aa and aa' mean a residue of an α-amino acid, whereby aa can be the same or different from aa'.

The present invention also relates to the pharmaceutically acceptable salts and esters of the compounds of the formula (I). Pharmaceutically acceptable salts, e.g. acid addition salts with both organic and inorganic acids are well known in the field of pharmaceuticals. Pharmaceutically acceptable esters, when applicable, may be prepared by known methods using pharmaceutically acceptable acids that are conventional in the field of pharmaceuticals and that retain the pharmacological properties of the free form.

The invention is also directed to a method for the preparation of the novel compounds of the formula (I). Such methods will be described in detail below. A further object of the invention is a pharmaceutical composition containing at least one pharmaceutically acceptable diluent, carrier, and/or excipient, as well as a therapeutically effective amount of a compound of the formula (1) as the active agent. Still a further object of the invention is the use of the compounds of the formula (I) as a prolyl oligopeptidase inhibitor, for example in the treatment of neurodegenerative diseases, such as for Alzheimer's disease, and senile dementia, as well as for improving learning and memory functions.

DETAILED DESCRIPTION OF THE INVENTION

In the above-mentioned formula (I), the symbols have the following meanings:

A straight or branched alkylene chain in the meaning of Q has 1 to 10 carbon atoms, where the linking chain preferably contains 2 to 4 carbon atoms. Such a group is optionally substituted with 1 to 3 substituent(s) each independetly being hydroxy, oxo, lower alkoxy, amino, lower alkyl amino, halogen, carboxyl or lower acyl.

A straight or branched alkenylene chain in the meaning of Q has 2 to 10 carbon atoms, where the linking chain preferably contains 2 to 4 carbon atoms. Such a group is optionally substituted with 1 to 3 substituent(s) as defined for the alkylene group above.

Arylene in the meaning of Q, or when incorporated as a chain member in an alkylene or alkenylene chain Q, preferably contains 6 to 12 carbon atoms and is preferably an optionally substituted monocyclic arylene, where the aromatic ring is preferably linked to the molecular structure of formula (I) from the meta or para positions. Such a group is optionally substituted with 1 to 3 substituent(s) each independently being lower alkyl, hydroxy, lower alkoxy, amino, lower alkyl amino, halogen, carboxyl or lower acyl. A preferred monocyclic arylene is phenylene, such as 1,3-phenylene.

A cycloalkylene or a cycloalkenylene group in the meaning of Q, or when incorporated as a chain member in an alkylene or alkenylene chain Q, has 3 to 10 carbon atoms, preferably 5 to 7 carbon atoms in the ring. Such a group is optionally substituted with 1 to 3 substituent(s) each independently being lower alkyl or as defined for the alkylene group above.

The alkyl group having 1 to 10 carbon atoms or the alkenyl group having 2 to 10 carbon atoms in the meaning of A is optionally substituted with 1 to 3 substituent(s) each independently being $COOR^1$, $COR^1$, $CR^1(OR^2)_2$, $COCH_2OR^3$, cyano, hydroxy, oxo, lower alkoxy, amino, lower alkyl amino, halogen or one of the structures:

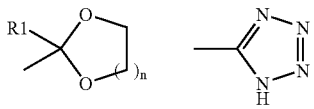

wherein $R^1$ is H, lower alkyl, lower alkenyl, cycloalkyl, cycloalkenyl, aryl or aralkyl, $R^2$ is lower alkyl, lower alkenyl, cycloalkyl, cycloalkenyl, aryl or aralkyl, $R^3$ is H, lower alkyl, lower acyl or halogen, and n is an integer from 1 to 4.

A carbocyclic ring in the meaning of A, or incorporated as a chain member in the alkyl or alkenyl group A, is a saturated or unsaturated 3 to 7 membered ring with only carbon atoms in the ring. Preferably it has 5 ring members. Such a group is optionally substituted with 1 to 3 substituent(s) each independently being lower alkyl or as defined for the alkyl group above.

A heterocyclic ring in the meaning of A, or incorporated as a chain member in the alkyl or alkenyl group A, preferably contains 1 to 3 heteroatoms selected from a nitrogen atom, an oxygen atom and/or a sulphur atom. Preferably it has five ring members. The heterocyclic group A is optionally substituted with 1 to 3 substituent(s) each independently being lower alkyl or as defined for the alkyl group above. An advantageous heterocyclic group A is the pyrrolidine ring linked from the nitrogen to the rest of the structure in formula (I). In this structure the pyrrolidine ring is preferably substituted at the 2-position.

When A is lower alkoxy, aryloxy, aryl lower alkoxy, lower alkyl amino, aryl amino or aryl lower alkyl amino group, the alkyl, aryl or arakyl subgroups are optionally substituted with 1 to 3 substituent(s) as defined for the alkyl group above.

E is preferably a bulky group. Thus for example isopropyl is preferred over methyl. Such a group is optionally substituted with 1 to 3 substituent(s) each independently being $COOR^1$, $COR^1$, $CR^1(OR^2)_2$, $COCH_2OR^3$, cyano, hydroxy, oxo, lower alkoxy, aryloxy, aryl lower alkoxy, amino, lower alkyl amino, aryl amino, aryl lower alkyl amino, halogen or one of the structures:

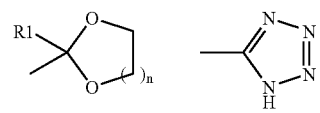

wherein $R^1$ is H, lower alkyl, lower alkenyl, cycloalkyl, cycloalkenyl, aryl or aralkyl, $R^2$ is lower alkyl, lower alkenyl, cycloalkyl, cycloalkenyl, aryl or aralkyl, $R^3$ is H, lower alkyl, lower acyl or halogen, and n is an integer from 1 to 4.

An alkenyl chain in the meaning of E preferably contains 2 to 10 carbon atoms and is optionally substituted with 1 to 3 substituent(s) as defined for the alkyl group, in the meaning of E, above.

A carbocyclic ring in the meaning of E, or incorporated as a group member in an alkyl or alkenyl group E, contains only carbon atoms. A carbocyclic ring E with 5 to 7 ring members is preferred as it is sufficiently bulky. Such a group is optionally substituted with 1 to 3 substituent(s) each independently being lower alkyl or as defined for the alkyl group, in the meaning of E, above.

A heterocyclic ring in the meaning of E, or incorporated as a group member in an alkyl or alkenyl group E, is optionally substituted with 1 to 3 substituent(s) each independently being lower alkyl or as defined for the alkyl group, in the meaning of E, above. The preferred ring size is 5 to 7 ring members.

When E is lower alkoxy, aryloxy, aryl lower alkoxy, lower alkyl amino, aryl amino or aryl lower alkyl amino group, the alkyl, aryl or aralkyl subgroups are optionally substituted with 1 to 3 substituent(s) each independently being lower alkyl or as defined for the alkyl group, in the meaning of E, above.

An amino functionality containing heterocyclic ring in the meaning of E' is preferably linked from the nitrogen to the rest of the structure in formula (I). Such a heterocyclic ring is optionally substituted with 1 to 3 substituent(s) each independently being $COOR^1$, $COR^1$, cyano, hydroxy, lower alkoxy, aryloxy, aryl lower alkoxy, amino, lower alkyl amino, aryl amino, aryl lower alkyl amino or halogen, wherein $R^1$ is H, lower alkyl, lower alkenyl, cycloalkyl, cycloalkenyl, aryl or aralkyl.

When E' is lower alkyl amino, aryl amino or aryl lower alkyl amino group, the alkyl, aryl or aralkyl subgroups are optionally substituted with 1 to 3 substituent(s) as defined for the heterocyclic group, in the meaning of E', above;

The α-amino acid residues aa and aa' are incorporated in the compound of formula (I) with a peptide bond to the central group. In this specification, the free amino acids corresponding to the groups aa and aa' would thus be denoted H-aa-OH and H-aa'-OH, respectively.

The α-amino acid residues aa and aa' can be the same or different. The preferred α-amino acid residues are L-prolyl, L-alanyl, L-methionyl and L-phenylalanyl. The preferred combination of aa and aa' is where they are both L-prolyl. The preference for L-prolyl is higher at aa than at aa'. Also other α-amino acid residues that mimic L-prolyl are possible, such as L-thioprolyl.

The compounds of the invention may be converted, if desired, into their pharmaceutically acceptable salt or ester form using methods well known in the art.

The various substituents and groups used in this specification are defined as follows.

"Lower alkyl" means a straight or branched hydrogen carbon chain having 1 to 7, preferably 1 to 5 carbon atom(s), and examples thereof include methyl, ethyl, propyl, isopropyl, butyl, sec-butyl, tert-butyl, and pentyl.

"Lower alkenyl" means a straight or branched unsaturated hydrogen carbon chain having 2 to 7, preferably 2 to 5 carbon atoms, and examples thereof include ethenyl, propenyl, butenyl and pentenyl.

"Lower alkoxy" as such or in the group "lower alkoxy carbonyl", is an alkoxy group having 1 to 7, preferably 1 to 5 carbon atom(s), and examples thereof include methoxy, ethoxy, propoxy, isopropoxy, butoxy, sec-butoxy, tert-butoxy and pentoxy. "Lower alkoxy carbonyl" is for example, methoxycarbonyl, ethoxycarbonyl, propoxycarbonyl, isopropoxycarbonyl, butoxycarbonyl, sec-butoxycarbonyl, and tert-butoxycarbonyl.

"Lower alkyl amino" is an alkyl or dialkyl amino having 1 to 7 carbon atom(s) in the alkyl group(s), and examples thereof include methyl amino, ethyl amino, propyl amino, isopropyl amino, butyl amino and pentyl amino.

"Lower acyl" is an acyl group having 2 to 7 carbon atoms, and examples thereof include acetyl, propanoyl, isopropanoyl, butanoyl, sec-butanoyl, tert-butanoyl and pentanoyl.

A "cycloalkyl" or a "cycloalkenyl group" in the meaning of $R^1$ and/or $R^2$ preferably has 5 to 7 carbon atoms in the ring.

A "heterocyclic ring" or a "heterocycloalkyl" group in the meaning of $R^1$ and/or $R^2$ preferably has 5 to 7 atoms in the ring and contains 1 to 3 heteroatom(s) selected from a nitrogen atom, an oxygen atom and/or a sulphur atom. Such a group is preferably derived from pyrrole, pyridine, azepine, furan, pyran, oxepine, thiophene, thiopyran, thiepine or their corresponding hydrated or partially hydrated derivatives.

"Aryl" as such or as a part of an "aralkyl", especially an "aryl lower alkyl" group, or as a part of an "aryloxy" or "aryl amino" preferably means an optionally substituted aromatic group with 6 to 12 carbon atoms, and is preferably a monocyclic aryl group, such as a phenyl group. The aryl group is optionally substituted with 1 to 3 substituent(s) each independently being lower alkyl or as defined for the alkylene group Q. The alkylene chain in aralkyl is preferably a lower alkylene chain and contains 1 to 5 atom(s).

"Halogen atom" means chlorine, bromine, fluorine or iodine.

Preferred compounds of the formula (I) wherein G is -aa'E are the compounds wherein Q is a branched or unbranched alkylene with 1 to 6 carbon atoms in the linking chain, or wherein Q is 1,4-phenylene, 1,3-phenylene or 1,2-phenylene, and A is methyl, cyclopentyl, 1-pyrrolidinyl, 2(S)-cyanopyrrolidin-1-yl, 2(S)-(hydroxyacetyl)pyrrolidin-1-yl, 2(S)-formylpyrrolidin-1-yl, 2(S)-(methoxycarbonyl)pyrrolidin-1-yl, 1-azepanyl or 4-morpholinyl, and E is a branched or unbranched alkyl with 1 to 10 carbon atoms, or wherein E is cyclopentyl, cyclohexyl, cycloheptyl, 1-pyrrolidinyl, 1-piperidinyl, 2(S)-cyanopyrrolidin-1-yl, 2(S)-(methoxycarbonyl)pyrrolidin-1-yl, 4-(tert-butoxycarbonyl)piperazin-1-yl, methoxy, 1-piperazinyl, 4-morpholinyl, 1-azepanyl, phenyl, benzyl or benzyl amino, and aa and aa' are independently L-prolyl, L-alanyl or L-methionyl, whereby aa can be the same or different from aa'.

Preferred compounds of the formula (I) wherein G is E' are the compounds wherein Q is a branched or unbranched alkylene with 1 to 6 carbon atoms in the linking chain, or wherein Q is 1,4-phenylene, 1,3-phenylene or 1,2-phenylene, and A is methyl, cyclopentyl, 1-pyrrolidinyl, 2(S)-cyanopyrrolidin-1-yl, 2(S)-(hydroxyacetyl)-pyrrolidin-1-yl, 2(S)-formylpyrrolidin-1-yl, 2(S)-(methoxycarbonyl)pyrrolidin-1-yl, 1-azepanyl or 4-morpholinyl, and E' is 1-pyrrolidinyl, 1-piperidinyl, 4-morpholinyl or 1-azepanyl, and aa is L-prolyl, L-alanyl or L-methionyl.

The compounds can be prepared according to following techniques.

The synthesis strategy is dependent on whether or not the compound is symmetrical. The compound is symmetrical with respect to G and aa-A, i.e. if the amino acid residues aa and aa' are the same and the groups A and E are the same.

The symmetrical case of formula (I) can therefore be described by formula (I') in Scheme 1. A' represents the groups, that are valid by the definitions of both A and E.

Scheme 1

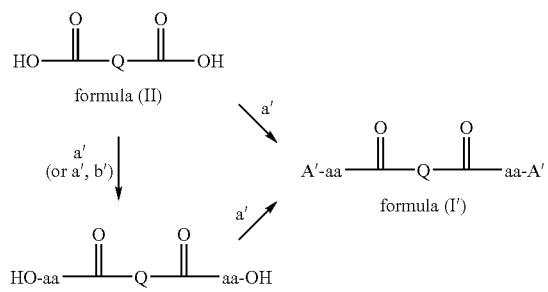

The symmetrical compounds of formula (I') can be prepared from the dicarboxylic acid of formula (II). The reactions a' and b' are variants of reactions a and b, respectively, which are described below. When the starting material is difunctional, the reaction is marked a' or b'. Reaction a is an amide bond (peptide bond) forming reaction. Reaction b is an ester hydrolysis reaction (the ester group is usually applied as a protecting group, such as an alkyl ester group of a carboxylic acid functionality).

A known method per se can be employed for the amide bond (or peptide bond) formation. Amide bonds can be prepared from an activated carboxylic acid and an amine. Examples of methods usable for the formation of the amide bond include methods using the corresponding acid chloride or anhydride, the mixed anhydride method, using dicyclohexylcarbodiimide (DCC) or another carbodiimide with or without additives, the activated ester method and the azide method.

Acid chlorides are either commercially available, or they are prepared from the corresponding acid with thionyl chloride at the temperature between 0 and 80° C. The used symmetrical acid anhydrides are commercially available. The acid chloride or acid anhydride are allowed to react with the amine at basic conditions, where the base can be triethylamine or another tertiary amine in an organic solvent, or NaOH, $Na_2CO_3$ or another inorganic base in an aqueous solution or an aqueous organic two-phase system.

In the mixed acid anhydride method, the amide bond is formed by a reaction of the free carboxylic acid with an acid chloride such as pivaloyl chloride, tosyl chloride or oxalyl chloride, or an acid derivative such as ethyl chloroformate or isobutyl chloroformate in an inert solvent in the presence of a tertiary amine such as triethylamine, at the temperature between −20 and 40° C. The reaction affords the mixed anhydride, which is then reacted with the amine to give the amide.

In the DCC method, the amide bonds are formed by reacting the carboxylic acid and the amine in an inert solvent using DCC or another suitable carbodiimide as the condensing agent in the presence of or absence of tertiary amine such as triethylamine, and with or without addition of suitable additive such as N-hydroxybenzotriazole.

According to the activated ester method, the amide bond is formed by activating the carboxylic acid with DCC or another suitable carbodiimide, in the presence of N-hydroxysuccimide, para-nitrophenol, thiophenol, or para-nitrothiophenol, with or without isolation of the active ester. The activated ester is then allowed to react with the amine, affording the amide.

In the azide method the azide is generated from the carboxylic acid under relatively mild condition. The procedure is esterification, treatment with hydrazine and finally with nitrous acid. The azide is then allowed to react with the amine, affording the amide.

The ester groups are usually used as protecting groups in amide bond forming reactions. They are also applied to improve the solubility of the compound in organic solvents (such as in proline methyl ester). Ester hydrolysis is performed in aqueous basic conditions. Usually methanol is added to the solvent in order to increase the solubility of the ester. Alkyl esters, especially methyl esters, are hydrolysed by LiOH or another alkali metal hydroxide in a methanol-water mixture.

The unsymmetrical compounds, where G is aa'-E and aa and aa' are different, and/or A and E are different, or where G is E' in formula (I), can be prepared by the synthesis routes in Schemes 2 and 3.

The starting compound in Scheme 2 is a monoprotected dicarboxylic acid (III) and that of Scheme 3 is a carboxylic acid activated as a symmetrical anhydride (IV). The reaction c is an amide bond forming reaction (see the description above for amide forming reactions). Two symmetrical products can also be obtained in Scheme 3.

The general strategy for the synthesis is the same for the groups aa-A and aa'-E. Therefore only the case of the group aa-A is presented below in Scheme 4.

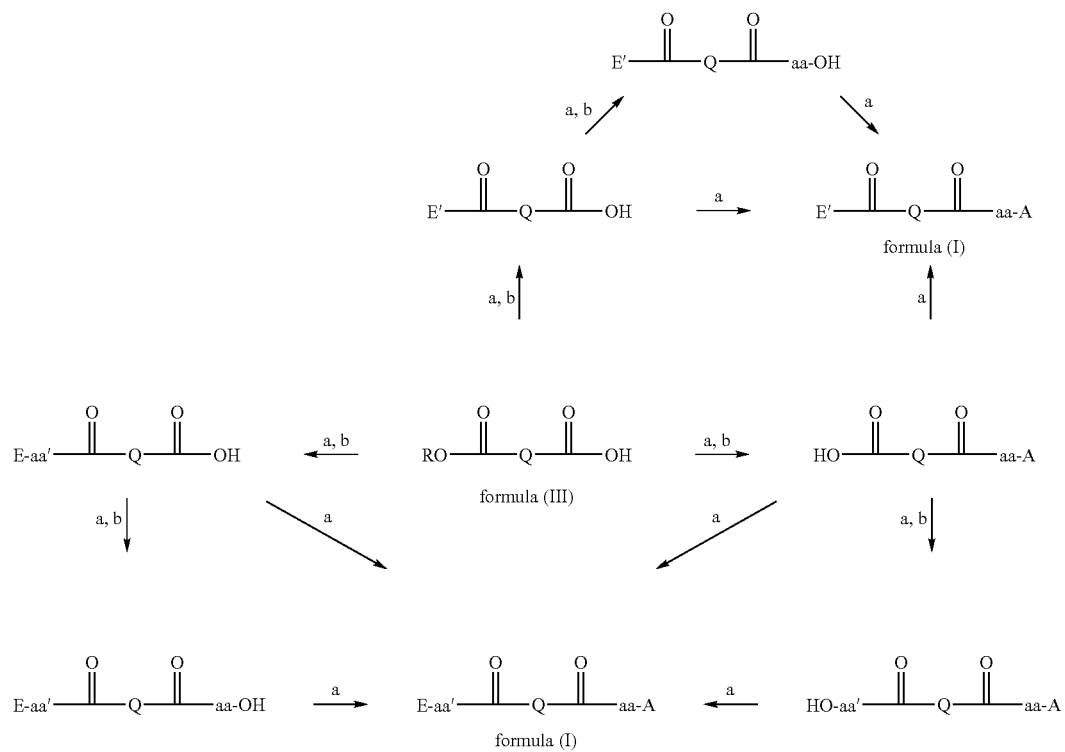

Scheme 3

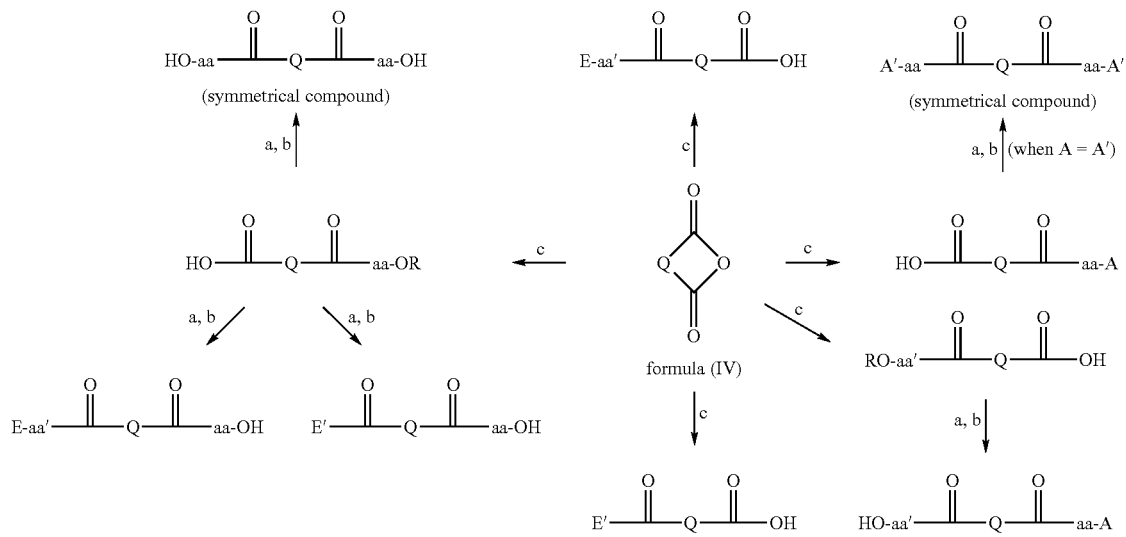

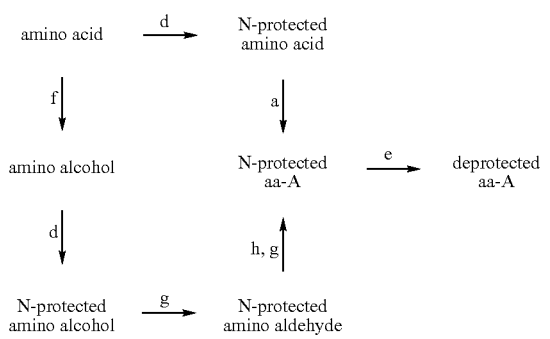

Scheme 4

The reaction route d, a and e gives an amide functionality between aa and A, and the route f, d, g, h, g and e gives a ketone functionality between aa and A. Reaction d is a protection of the amino group. Reaction e is the removal of the amino protection group. Reaction f is the reduction of the amino acid to the corresponding amino alcohol. Reaction g is an oxidation of a primary or secondary alcohol functionality to an aldehyde or ketone, respectively. Reaction h is a Grignard reaction.

The amino functionality is protected by a suitable protecting group using known methods from literature. A preferred protecting group is tert-butoxy carbonyl group (BOC). The removal of these protecting groups is also performed by well-known methods.

The amino acid is reduced to the corresponding amino alcohol by refluxing it with $LiAlH_4$ in anhydrous THF.

The Grignard reaction is performed by treating the N-protected aldehyde with a Grignard regent at −80 to −40° C. An excess of Grignard regent is destroyed with aqueous ammonium chloride before reaching room temperature. The reaction affords a secondary alcohol.

Oxidation of primary or secondary alcohols to aldehydes and ketones, respectively, can be performed by known methods for these two types of oxidations, such as different types of dimethyl sulfoxide (DMSO) oxidations at basic conditions with $SO_3$-pyridine, oxalyl chloride or TFAA or methods using chromic oxide.

For the formation of a salt with the compounds of the formula (I) any suitable, pharmaceutically acceptable acid or base can be used, such as hydrochloric, hydrobromic, sulphuric, phosphoric or nitric acid, or an organic acid, such as acetic acid, propionic, succinic, glycolic, lactic, maleic, malonic, tartaric, citric, fumaric, methanesulfonic, p-toluene sulfonic and ascorbic acid, as well as salts with amino acids, such as aspartic and glutamic acid. Suitable inorganic bases are, for example, the alkali, earth alkaline metal or ammonium hydroxides and carbonates, as well as organic bases, such as organic amines, for example trialkyl amines, pyridine etc.

The novel compounds according to the invention may be used to treat any condition, which responds to a treatment with a prolyl oligopeptidase inhibitor. The compound according to the invention can be administered for example orally, parenterally, topically or rectally by means of any pharmaceutical formulation useful for said administration, and containing the said compound in pharmaceutically acceptable and effective amounts together with pharmaceutically acceptable carriers, adjuvants or vehicles known in the art. The manufacture of such pharmaceutical formulations is well known in the art.

Thus the pharmaceutical composition may be in a dosage form suitable for oral use, such as tablets, capsules, liquid dosage forms, e.g. as suspensions, emulsions, syrups etc. All such formulations are made using per se known formulation techniques and carriers, adjuvants and additives. The compounds according to the invention may also be administered parenterally, e.g. for infusion and injection, for example using aqueous or oily suspensions, emulsions, or dispersions containing the active agent in combination with conventional pharmaceutically acceptable excipients. Formulations for rectal use are e.g. suppositories containing the active prodrug in combination with carrier substances suitable for rectal use.

The therapeutic dose to be given to a patient in need of treatment will vary depending on the body weight and age of the patient, the particular condition being treated, as well as the manner of administration, and are easily determined by a person skilled in the art. Typically a dosage form for oral use containing 0.1 mg to 5 g, typically 0.1 mg to 500 mg of active agent to be administered 1 to 3 times daily, would be suitable for most purposes.

The following examples illustrate the invention without limiting the same in any way.

GENERAL SYNTHESIS PROCEDURES

Procedure A: Amide Formation Using Mixed Anhydride Method

A solution of 1.0 mmol pivaloyl chloride in dichloromethane is added to a solution of 1.0 mmol carboxylic acid (or 0.5 mmol dicarboxylic acid) and 1.1 mmol triethyl amine in dichloromethane at 0° C. The reaction mixture is stirred at 0° C. for 1 h. A solution of 1.1 mmol triethyl amine and 1.0–1.1 mmol amine in dichloromethane is slowly added at 0° C. (if the amine is in the form of a trifluoroacetic acid salt or HCl salt, then 3.3 mmol triethyl amine is used and the triethyl amine is added separately before the addition of the amine). The reaction mixture is stirred 2 h or overnight at room temperature (rt). The dichloromethane solution is washed with 30% citric acid aq, saturated NaCl aq and saturated NaHCO$_3$ aq. The dichloromethane phase is dried with anhydrous Na$_2$SO$_4$ and evaporated, yielding the crude product.

Procedure B: Amide Formation Using DCC-Method

A solution of 1.0 mmol N,N'-dicyclohexylcarbodiimide in acetonitrile is added to a solution of 1.0 mmol carboxylic acid and 1.0 mmol N-hydroxysuccinimide in acetonitrile at −20° C. The reaction mixture is stirred at −20° C. for 1 h, and then left without stirring at −20° C. overnight. The formed N,N'-dicyclohexylurea is filtered off, and the filtrate is evaporated. The residue is scraped with hexane, and the hexane is decanted or filtered off. The residue is finally evaporated in vacuo yielding the activated ester. A solution of 1.0 mmol amine in anhydrous tetrahydrofuran is added slowly to a solution of 1.0 mmol activated ester in anhydrous tetrahydrofuran at rt. The reaction mixture is stirred at rt for 4–48 h. The solvent is evaporated and the residue is dissolved in dichloromethane. The dichloromethane solution is washed with 30% citric acid aq, saturated NaCl aq, and saturated NaHCO$_3$ aq. The dichloromethane phase is dried with anhydrous Na$_2$SO$_4$ and evaporated yielding the crude product.

Procedure C: Amide Formation of Amino Acids and Acid Chlorides

A solution of 1.0 mmol dicarboxylic acid dichloride in a suitable organic solvent (diethyl ether, chloroform, dichloromethane) is added to a solution of 2.0 mmol amino acid and 4.0–4.8 mmol NaOH in water at 0° C. while stirring vigorously. The reaction is stirred 1–24 h at rt. The organic phase is separated and the water phase is made acidic with aqueous HCl. The water phase is evaporated and the residue is dissolved in dichloromethane (or chloroform). A small modification of the procedure is that the product is extracted from the acidified aqueous phase with 25–50% ethanol in chloroform (or in dichloromethane). In both cases the organic layer is dried with anhydrous Na$_2$SO$_4$ and evaporated yielding the product.

Procedure D: Amide Formation Using Acid Chloride

A solution of 1.0 mmol dicarboxylic acid dichloride in a suitable solvent (dichloromethane, diethyl ether) is mixed with a solution of 2.0 mmol amine in a suitable organic solvent (dichloromethane, diethyl ether) in the presence of aqueous solution of 2 ml 4 M NaOH at 0° C. while stirring vigorously (if the amine is in the form of trifluoroacetic acid salt or HCl salt then 6 ml 4 M NaOH is used). The reaction is stirred vigorously for 1–2 h at rt. Dichloromethane is added and the phases are separated. The organic phase is washed with saturated NaCl aq. The organic phase is dried with anhydrous Na$_2$SO$_4$ and evaporated yielding the crude product.

Procedure E: Protecting an Amino Functionality with BOC

A solution of 1.1 mmol di-tert-butyl dicarbonate in diethyl ether is added to a solution of 1.0 mmol amino acid in 1.15 ml (2.3 mmol) 2 M NaOH aq at 0° C. The reaction is stirred vigorously for 4 h or overnight at rt. Water is added and the ether phase is removed. The aqueous phase is washed with diethyl ether. The aqueous phase is made acidic with aqueous HCl, and the aqueous phase is extracted with ethyl acetate. The ethyl acetate phase is washed with water and saturated NaCl aq. The ethyl acetate phase is dried with anhydrous Na$_2$SO$_4$ and evaporated yielding the product.

Procedure F: Grignard Reaction

2–3 mmol alkylmagnesium chloride (or another suitable Grignard reagent) in diethyl ether or tetrahydrofuran is added to a solution of 1.0 mmol of a protected amino aldehyde, e.g. BOC-L-prolinal in 3 ml anhydrous tetrahydrofuran at −80–60° C. The reaction was allowed to proceed 30–60 min at −80–40° C., and then the reaction is stopped by adding 1.0–1.5 ml saturated NH$_4$Cl aq. The reaction mixture is warmed to rt, and water and ethyl acetate are added. The product is extracted with ethyl acetate from the aqueous phase. The organic phase is washed with 30% citric acid aq, saturated NaCl aq and saturated NaHCO$_3$ aq. The organic phase is dried with Na$_2$SO$_4$ and evaporated yielding the crude product.

Procedure G: Oxidation of Alcohol

A solution of 3 mmol sulphur trioxide pyridine complex in 3 ml anhydrous dimethyl sulfoxide is added slowly to a solution of 1 mmol of primary (or secondary) alcohol and 3 mmol triethyl amine in 3 ml anhydrous dimethyl sulfoxide at rt. The reaction is stirred 2 h at rt, and then the reaction mixture is poured into 30 ml ice water. The product is extracted from the aqueous phase with dichloromethane (or chloroform). The organic phase is washed with 30% citric acid aq, saturated NaCl aq and saturated NaHCO$_3$ aq. The organic phase is dried with Na$_2$SO$_4$ and evaporated yielding the crude product.

Procedure H: Hydrolysis of Carboxylic Acid Methyl Ester 1.0–1.5 mmol LiOH.H$_2$O is added to a solution of 1.0 mmol of e.g. carboxylic acid methyl ester in 25% water in methanol. The reaction is stirred overnight or longer at rt. The solvent (methanol) is evaporated and the residue is dissolved in water. The aqueous phase is washed with dichloromethane. The aqueous phase is made acidic with 2–3 M HCl aq, and the product is extracted with dichloromethane. The organic phase is dried with anhydrous Na$_2$SO$_4$ and evaporated yielding the product.

Procedure I: Hydrolysis of an O-acetyl Group 1.1 mmol K$_2$CO$_3$ is added very slowly to a solution of 1.0 mmol acetoxyacetyl compound in 6 ml 50% methanol in water at 0° C. The reaction is stirred 10 min after the addition in 0° C., and then 50 min at rt. The methanol is evaporated. 75 ml dichloromethane and 30 ml of saturated NaCl aq is added, and then the phases are separated. The dichloromethane phase is washed once more with saturated NaCl aq. The dichloromethane phase is dried with anhydrous Na$_2$SO$_4$ and evaporated yielding the crude product.

Procedure J: Removal of BOC Protecting Group

2–4 ml ethyl acetate saturated with dry HCl is added to 1.0 mmol BOC protected amine at rt. The reaction mixture is stirred at rt for 30 min. Another way to proceed is to dissolve 1.0 mmol BOC protected amine in 5–10 ml dichloromethane and add 2–4 ml trifluoroacetic acid at 0° C. The reaction is stirred at 0° C. for 2–2.5 h. In both cases the solvent is removed and the product is finally evaporated in vacuo yielding the corresponding amine HCl salt or trifluoroacetic acid salt, respectively.

PREPARATION OF STARTING MATERIALS

L-Proline methyl ester HCl salt 16 ml (220 mmol) thionyl chloride was added to a solution of 10 g (87 mmol) L-proline in 200 ml methanol at 0° C. The reaction mixture is refluxed for 1 h. The solvent was evaporated. Yield 14 g (86 mmol, 99%).

BOC-L-alanine 5.0 g (56.1 mmol) L-alanine was BOC protected according to procedure E. Yield 10.0 g (52.85 mmol, 94%)

BOC-L-proline 5.0 g (43.4 mmol) L-proline was BOC protected according to procedure E. Yield 8.84 g (41.1 mmol, 95%)

BOC-L-alanyl-pyrrolidine 10.0 g (53 mmol) BOC-alanine was coupled to 8.7 ml (105 mmol) pyrrolidine according to procedure B. Yield of active ester 14.97 g (52 mmol, 98%). Yield of crude product 10.97 g. The product was purified by a silica column using 50–100% ethyl acetate in petroleum ether as eluent. Yield 9.07 g (37.4 mmol, 72%).

BOC-L-prolyl-pyrrolidine 7.97 g (37.0 mmol) BOC-L-proline and 3.09 ml (37.0 mmol) pyrrolidine were coupled according to procedure A. Yield of crude product 11.9 g. The product was purified with a silica column using 2.5–5% methanol in dichloromethane as eluent. Yield 8.31 g (31.0 mmol 84%).

BOC-L-prolyl-L-proline methyl ester 2.15 g (10 mmol) BOC-L-proline and 1.66 g (10 mmol) proline methyl ester HCl salt were coupled according to procedure A. Yield of crude product 2.83 g. The product was purified with a silica column using 5% methanol in ethyl acetate as eluent. Yield 2.40 g (7.4 mmol, 74%)

BOC-L-prolyl-amide 1.91 ml (20 mmol) ethyl chloroformate was added to a solution of 4.31 g (20 mmol) BOC-L-proline and 2.79 ml (20 mmol) triethyl amine in 40 ml tetrahydrofuran at −10° C. The reaction was kept in −10° C. for 20 min. 5.1 ml 25% NH$_3$ aq was added to the reaction at −10° C. The reaction mixture was left at rt overnight. The solvent was evaporated. The residue was dissolved in ethyl acetate and filtered. The filtrate was dried with anhydrous Na$_2$SO$_4$ and evaporated. Yield of crude product 5.13 g. The product was purified with a silica column using 5% methanol in ethyl acetate as eluent. Yield 4.05 g (18.9 mmol, 95%).

BOC-2(S)-cyanopyrrolidine 2.89 ml (20.8 mmol) trifluoroacetic acid anhydride was added to a solution of 4.05 g (18.9 mmol) BOC-L-prolyl-amide and 5.80 ml (41.6 mmol) triethyl amine in tetrahydrofuran at 0° C. The reaction was kept at rt for 2 h. 20 ml water was added, and the reaction was evaporated. The residue was dissolved in dichloromethane, and the organic phase was washed with 0.1 M HCl aq and 0.1 M NaOH aq. The organic phase was dried with anhydrous Na$_2$SO$_4$ and evaporated. Yield of crude product 3.64 g. The product was purified with a silica column using 25% ethyl acetate in petroleum ether as eluent. Yield 3.37 g (17.2 mmol, 91%).

BOC-2(S)-(diazoacetyl)pyrrolidine

The solutions of 0.4 g (7 mmol) KOH in 10 ml anhydrous ethanol and 2.14 g (10 mmol) N-methyl-N-nitroso-4-toluenesulfonamide in 30 ml diethyl ether were mixed in the reactor tube of the diazomethane distillation apparatus at 0° C. The reactor tube was kept 5 min at 0° C., and then it was placed into a 60° C. oil bath. The distillation was stopped when about 25 ml of diethyl ether containing the diazomethane was distilled over. The reaction was carried out three times for the next step. 3.14 ml (33 mmol) ethyl chloroformate was added to a solution of 6.46 g (30 mmol) BOC-L-proline and 4.60 ml (33 mmol) triethyl amine in 100 ml tetrahydrofuran at −20° C. The reaction mixture was stirred at −20° C. for 30 min. Then 75 ml diazomethane in ether (containing maximum 0.30 mmol diazomethane) was added to the reaction mixture at −20° C. The reaction mixture was stirred for 1 h at −20° C., and the flask was kept without stirring at −20° C. overnight. 120 ml toluene was added, and the organic phase was washed with saturated NaHCO$_3$ aq and water. The organic phase was dried with anhydrous Na$_2$SO$_4$ and evaporated. Yield of crude product 8.3 g.

BOC-2(S)-acetoxyacetyl)pyrrolidine 8.3 g crude BOC-2(S)-(diazoacetyl)pyrrolidine and 30 ml acetic acid was stirred at 100° C. for 10 min. The reaction mixture was evaporated. The residue was dissolved in ethyl acetate and the solution was washed with saturated NaHCO$_3$ aq and water. The ethyl acetate phase was dried with anhydrous Na$_2$SO$_4$ and evaporated. Yield of crude product 3.76 g. The product was purified with a silica column using 20% ethyl acetate in petroleum ether as eluent. Yield 1.94 g (7.2 mmol, 24% calculated from BOC-L-proline)

L-Prolinol 17.3 g (150 mmol) L-proline was added to a suspension of 8.5 g (225 mmol) LiAlH$_4$ in 250 ml anhydrous tetrahydrofuran at 0° C. The reaction mixture was refluxed 2 h. After cooling to rt, the excess of LiAlH$_4$ was destroyed with 18 ml 20% KOH aq. The reaction mixture was filtered and the residue was refluxed with new tetrahydrofuran for 30 min. The reaction mixture was filtered. The combined tetrahydrofuran layers were dried with anhydrous Na$_2$SO$_4$ and evaporated. Yield 14.6 g (144 mmol, 96%).

BOC-L-prolinal

A solution of 31.4 g (144 mmol) di-tert-butyl dicarbonate in dichloromethane was added to a solution of 14.6 g (144 mmol) L-prolinol and 22.1 ml (159 mmol) triethyl amine in dichloromethane at 0° C. The reaction was left overnight at rt. The dichloromethane phase was washed with 30% citric acid aq, saturated NaCl aq and saturated NaHCO$_3$ aq. The organic phase was dried with Na$_2$SO$_4$ and evaporated. Yield 27.71 g (138 mmol, 96%). 27.71 g (138 mmol) BOC-L-prolinol was oxidized to the corresponding aldehyde according to procedure G. Yield of crude product 22.63 g. The product was purified with a silica column using 20% ethyl acetate in petroleum ether as eluent. Yield 18.4 g (92 mmol, 67%).

BOC-2(S)-(cyclopentanecarbonyl)pyrrolidine 22.5 ml (45 mmol) 2 M cyclopentylmagnesium chloride (diethyl ether) and 3.0 g (15 mmol) BOC-L-prolinal were allowed to react at −80° C. for 30 min according to procedure F. Yield of crude product 3.37 g. The product was purified with a silica column using 0–4% methanol in dichloromethane as eluent. Yield 3.10 g (11.5 mmol, 77%). The product was oxidized to the corresponding ketone according to procedure G. Yield of crude product 3.12 g. The product was purified with a silica column using 16% ethyl acetate in petroleum ether as eluent. Yield 1.3 g (4.9 mmol, 42%).

BOC-2(S)-benzoylpyrrolidine 10 ml (20 mmol) 2 M phenylmagnesium chloride (tetrahydrofuran) and 1.99 g (10 mmol) BOC-L-prolinal were allowed to react at −60–40° C. for 60 min according to procedure F. Yield of the crude product 3.06 g. The product was purified with a silica column using 16% ethyl acetate in petroleum ether as eluent. Yield 2.18 g (7.6 mmol, 76%). The product was oxidized to the corresponding ketone according to procedure G. Yield of crude product 3.15 g. The product was purified with a silica column using 20–25% ethyl acetate in petroleum ether as eluent. Yield 1.65 g (6.0 mmol, 79%).

BOC-2(S)-acetylpyrrolidine 25 ml (75 mmol) 3 M methylmagnesium chloride (diethyl ether) and 8.25 g (41.4 mmol) BOC-L-prolinal were allowed to react at −80° C. for 30 min according to procedure F. Yield of the crude product 9.19 g. The product was purified with a silica column using 33% ethyl acetate in petroleum ether as eluent. Yield 7.54 g (35.0 mmol 85%). The product was oxidized to the corresponding ketone according to procedure G. Yield of crude product 6.91 g. The product was purified with a silica column using 20–25% ethyl acetate in petroleum ether as eluent. Yield 5.61 g (26.3 mmol, 75%).

Isophthalic acid mono-methyl ester

A solution of 12.18 g (60 mmol) isophthaloyl chloride in 60 ml dichloromethane was added to 60 ml anhydrous methanol at 0° C. The reaction was left overnight at rt. The reaction mixture was evaporated and the residue was dissolved in dichloromethane. The organic phase was washed twice with saturated $NaHCO_3$ aq. The dichloromethane phase was dried and evaporated. Yield 11.05 g (56.9 mmol, 95%). A solution of 11.05 g (56.9 mmol) of isophthalic acid dimethyl ester and 2.39 g (56.9 mmol) $LiOH.H_2O$ in 150 ml anhydrous methanol was stirred for 4 d at rt The solvent was evaporated and the product was dissolved in water. The aqueous phase was washed with dichloromethane. The aqueous phase was made acidic with 2 M HCl aq. The product precipitated from the aqueous phase. The product was filtered off and dried in vacuo. The product was dissolved in 200 ml dry ethanol, and thereafter 600 ml water was added slowly while stirring. The product precipitated slowly overnight at +4° C. The product was filtered and dried in vacuo. Yield 8.32 g (46.2 mmol, 81%)

Isophthalic acid mono-(L-prolyl-pyrrolidine)amide 8.3 g (30.9 mmol) BOC-L-prolyl-pyrrolidine was deprotected using 50 ml HCl saturated ethyl acetate according to procedure J. 5.6 g (30.9 mmol) isophthalic acid monomethyl ester and the L-prolyl-pyrrolidine HCl salt were coupled according to procedure A. Yield of crude product 10.70 g. The product was purified with a silica column with 5–10% methanol in ethyl acetate as eluent. Yield 5.6 g (16.9 mmol, 55%). The methyl ester group of the product was hydrolysed using 782 mg (18.6 mmol) $LiOH.H_2O$ according to procedure H. Yield 5.07 g (15.3 mmol, 91%).

Isophthalic acid (L-proline methyl ester) L-prolyl-pyrrolidine amide 5.07 g (16.0 mmol) isophthalic acid mono-L-prolyl-pyrrolidine amide and 2.65 g (16.0 mmol) proline methyl ester HCl salt were coupled according to procedure A. Yield of crude product 6.53 g. The product was purified with a silica column using 15% methanol in ethyl acetate as eluent. Yield 4.19 g (9.8 mmol, 61%).

Isophthalic acid L-proline L-prolyl-pyrrolidine amide 4.19 g (9.8 mmol) isophthalic acid (L-proline methyl ester) L-prolyl-pyrrolidine amide was hydrolysed using 452 mg (10.8 mmol) $LiOH.H_2O$ according to procedure H. Yield 3.24 g (7.9 mmol, 81%).

Isophthalic acid nono-2(S)-(cyclopentanecarbonyl)pyrrolidine amide 1.3 g (4.9 mmol) BOC-2(S)-(cyclopentanecarbonyl)pyrrolidine was deprotected using 8.7 ml trifluoroacetic acid in 100 ml dichloromethane according to procedure J. 0.88 g (4.9 mmol) isophthalic acid monomethyl ester and the 2(S)-(cyclopentanecarbonyl)pyrrolidine trifluoroacetic acid salt were coupled according to procedure A. Yield of crude product 1.66 g. The methyl ester group of the product was hydrolysed using 317 mg (7.6 mmol) $LiOH.H_2O$ according to procedure H. Yield 1.28 g (4.1 mmol, 84%).

Isophthalic acid 2(S)-(cyclopentanecarbonyl)pyrrolidine (L-proline methyl ester) amide 1.28 g (4.1 mmol) isophthalic acid mono-2(S)-(cyclopentanecarbonyl)pyrrolidine amide and 0.75 g (4.5 mmol) proline methyl ester HCl salt were coupled according to procedure A. Yield of crude product 1.88 g. The product was purified with a silica column using ethyl acetate as eluent. Yield 1.19 g (2.8 mmol, 68%).

Isophthalic acid 2(S)-(cyclopentanecarbonyl)pyrrolidine L-proline amide 890 mg (2.1 mmol) isophthalic acid (L-proline methyl ester) 2(S)-(cyclopentanecarbonyl)pyrrolidine amide was hydrolysed using 131 mg (3.1 mmol) $LiOH.H_2O$ according to procedure H. Yield 870 mg (2.1 mmol, 100%).

Isophthalic acid mono-2(S)-acetylpyrrolidine amide 2.1 g (9.7 mmol) BOC-2(S)-acetylpyrrolidine was deprotected using 19.4 ml trifluoroacetic acid in 100 ml dichloromethane according to procedure J. 1.75 g (9.7 mmol) isophthalic acid monomethyl ester and the 2(S)-acetylpyrrolidine trifluoroacetic acid salt were coupled according to procedure A. Yield of crude product 2.66 g. The methyl ester group of the product was hydrolysed using 608 mg (14.5 mmol) $LiOH.H_2O$ according to procedure H. Yield 1.33 g (5.1 mmol, 52%).

Isophthalic acid 2(S)-acetylpyrrolidine L-proline amide 1.33 g (5.1 mmol) isophthalic acid mono-2(S)-acetylpyrrolidine amide and 840 mg (5.1 mmol) proline methyl ester HCl salt were coupled according to procedure A. Yield of crude product 1.77 g. The methyl ester group of the product was hydrolysed using 300 mg (7.1 mmol) $LiOH.H_2O$ according to procedure H. Yield 1.06 g (3.0 mmol, 59%).

Phthalic acid mono-(L-proline methyl ester)amide 6.7 g (45 mmol) phthalic acid anhydride was added to a solution of 7.4 g (45 mmol) L-proline methyl ester HCl salt and 13.8 ml (99 mmol) triethyl amine in dichloromethane at 0° C. The reaction mixture was stirred 4 h at rt. The organic phase was extracted with saturated $NaHCO_3$ aq. The aqueous phase was made acidic with 3 M HCl aq. The acidic aqueous phase was extracted with chloroform. The chloroform phase was dried with anhydrous $Na_2SO_4$ and evaporated. Yield 6.53 g (23 mmol, 51%).

Phthalic acid L-proline pyrrolidine amide 4.25 g (17.0 mmol) phthalic acid mono-(L-proline methyl ester)amide and 1.6 ml (18.7 mmol) pyrrolidine were coupled according to procedure A. Yield of crude product 5.8 g. The product was purified with a silica column using 5–20% methanol in ethyl acetate as eluent. Yield 4.77 g (14.4 mmol, 85%). The methyl ester group of the product was hydrolysed using 906 mg (21.6 mmol) $LiOH.H_2O$ according to procedure H. Yield 3.42 g (10.8 mmol, 75%).

Succinic acid di-L-proline amide 1.10 ml (10.0 mmol) succinyl dichloride (diethyl ether) and 2.3 g (20.0 mmol) L-proline were coupled according to procedure C, using 40.0 mmol NaOH. Yield 1.40 g (4.5 mmol, 45%).

Succinic acid mono-(L-prolyl-pyrrolidine)amide 1.98 g (7.4 mmol) BOC-L-prolyl-L-pyrrolidine was deprotected using 30 ml HCl saturated ethyl acetate according to procedure J. 980 mg (7.4 mmol) succinic acid mono-methyl ester and the L-prolyl-L-pyrrolidine HCl salt were coupled according to procedure A. Yield of crude product 2.74 g. The product was purified with a silica column using 5-10% methanol in ethyl acetate as eluent. Yield 1.81 g (6.4 mmol, 86%).

Glutaric acid mono-hexamethyleneimine amide 2.3 g (20 mmol) glutaric acid anhydride was added to a solution of 4.5 ml (40 mmol) hexamethyleneimine in 15 ml tetrahydrofuran. The solution was stirred for 2 d at rt. The reaction mixture was evaporated, dissolved in an aqueous NaOH solution and washed with dichloromethane. The aqueous phase was acidified with 3 M HCl aq and the product was extracted with dichloromethane. The combined organic phases were dried with anhydrous $Na_2SO_4$ and evaporated. Yield 1.61 g (7.5 mmol, 38%).

Glutaric acid hexamethyleneimine L-proline amide 1.61 g (7.5 mmol) glutaric acid mono-hexamethyleneimine amide and 1.24 g (7.5 mmol) L-proline methyl ester HCl salt were coupled according to procedure A. Yield of crude product 2.1 g. The product was purified with a silica column using 5–10% methanol in ethyl acetate as eluent. Yield 1.8 g (5.6 mmol, 74%). The methyl ester group of the product was hydrolysed using 350 mg (8.3 mmol) $LiOH.H_2O$ according to procedure H. Yield 1.55 g (5.0 mmol, 90%).

SYNTHESIS OF THE PRODUCT COMPOUNDS

Decoupled $^{13}$C-NMR was measured in $CDCl_3$. Some of the carbons give two (or more) peaks, due to amide bond rotamers (the amide bond on the amino side of proline). These additional peaks are only observed for proline and not for other amino acid residues. Some of the peaks are completely overlapping, and such a peak is reported as one peak in the list. Mass analysis was performed with an ESI-MS instrument. Elemental analysis is reported as the molecular formula when the values are within ±0.4% for C, H and N.

EXAMPLE 1

Succinic acid di-(L-prolyl-pyrrolidine)amide 780 mg (2.5 mmol) succinic acid di-L-proline amide and 0.42 ml (5.0 mmol) pyrrolidine were coupled according to procedure A. Yield of crude product 1.12 g. The product was purified with a silica column using 40% methanol in ethyl acetate as eluent. Yield 520 mg (1.2 mmol, 49%).

$^{13}$C-NMR: 24.11, 24.67, 26.21, 28.80, 28.87, 45.90, 46.22, 47.15, 57.83, 170.69. MS: 419 (M+1). Anal. ($C_{22}H_{34}N_4O_4.1.4 H_2O$) C, H, N.

EXAMPLE 2

Adipic acid di-L-proline amide 1.45 ml (10.0 mmol) adipoyl dichloride (diethyl ether) and 2.3 g (20.0 mmol) L-proline were coupled according to procedure C, using 40.0 mmol NaOH. Yield 1.15 g (3.4 mmol, 34%).

Adipic acid di-(L-prolyl-pyrrolidine)amide 850 mg (2.5 mmol) adipic acid di-L-proline amide and 0.42 ml (5.0 mmol) pyrrolidine were coupled according to procedure A. Yield of crude product 1.16 g. The product was purified with a silica column using 40% methanol in ethyl acetate as eluent. Yield 650 mg (1.5 mmol, 60%).

$^{13}$C-NMR: 24.14, 24.29, 24.84, 26.21, 28.87, 34.26, 45.87, 46.28, 47.28, 57.63, 170.75, 171.38. MS: 447 (M+1). Anal. ($C_{24}H_{38}N_4O_4.1.0H_2O$) C, H, N.

EXAMPLE 3

Glutaric acid di-(L-prolyl-L-proline methyl ester)amide 1.21 g (3.70 mmol) BOC-L-prolyl-L-proline methyl ester was deprotected using 15 ml HCl saturated ethyl acetate according to procedure J. A solution of 0.24 ml (1.85 mmol) glutaryl dichloride in dichloromethane was added to a solution of the L-prolyl-proline methyl ester HCl salt and 3.1 ml (22.2 mmol) triethyl amine in dichloromethane at 0° C. while stirring. The reaction mixture was stirred overnight at rt. The dichloromethane solution was washed with 30% citric acid aq, water and saturated $NaHCO_3$ aq. The dichloromethane phase was dried with anhydrous $Na_2SO_4$ and evaporated. Yield of crude product 850 mg. The product was purified with a silica column using 20–40% methanol in ethyl acetate as eluent. Yield 550 mg (1.0 mmol, 54%).

$^{13}$C-NMR: 19.67, 24.71, 24.98, 28.46, 28.84, 33.40, 46.64, 47.33, 52.12, 57.57, 58.68, 170.93, 171.50, 172.93. MS: 549 (M+1). Anal. ($C_{27}H_{40}N_4O_8.0.6 H_2O$) C, H, N.

EXAMPLE 4

Glutaric acid di-L-proline amide 1.28 ml (10.0 mmol) glutaryl dichloride (chloroform) and 2.30 g (20.0 mmol) L-proline were coupled according to procedure C, using 1.92 g (48 mmol) NaOH and dissolving the residue in chloroform. Yield 1.71 g (5.2 mmol, 52%).

Glutaric acid di-(L-prolyl-pyrrolidine)amide 1.31 g (4.0 mmol) glutaric acid di-(L-proline)amide and 0.67 ml (8.0 mmol) pyrrolidine were coupled according to procedure A. Yield of crude product 1.54 g. The product was purified with a silica column using 33% methanol in ethyl acetate as eluent. Yield 560 mg (1.3 mmol, 32%).

$^{13}$C-NMR: 19.80, 24.08, 24.81, 26.16, 28.86, 33.28, 45.86, 46.24, 47.32, 57.69, 170.65, 171.27. MS: 433 (M+1). Anal. ($C_{23}H_{36}N_4O_4.0.7 H_2O$) C, H, N.

EXAMAPLE 5

Succinic acid mono-(L-prolyl-pyrrolidine)amide

The methyl ester group of 750 mg (2.7 mmol) succinic acid methyl ester L-prolyl-pyrrolidine amide was hydrolysed using 170 mg (4.1 mmol) LiOH.H$_2$O according to procedure H. Yield 360 mg (1.3 mmol, 45%).

Succinic acid L prolyl-pyrrolidine pyrrolidine amide 0.36 g (1.3 mmol) succinic acid mono(L-prolyl-pyrrolidine)amide and 0.11 ml (1.3 mmol) pyrrolidine were coupled according to procedure A. Yield of crude product 230 mg. The product was purified with a silica column using 25% methanol in ethyl acetate as eluent. Yield 170 mg (0.53 mmol, 41%).

$^{13}$C-NMR: 24.12, 24.40, 24.76, 26.05, 26.22, 28.86, 29.16, 29.32, 45.66, 45.90, 46.25, 46.42, 47.26, 57.81, 170.50, 170.72, 170.78. MS: 322 (M+1). Anal. (C$_{17}$H$_{27}$N$_3$O$_3$) C, H, N.

EXAMPLE 6

Succinic acid di-(L-prolyl-hexamethyleneimine)amide 880 mg (2.75 mmol) succinic acid di-L-proline amide and 0.62 ml (5.5 mmol) hexamethyleneimine were coupled according to procedure A. Yield of crude product 1.11 g. The product was purified with a silica column using 20–33% methanol in ethyl acetate as eluent. Yield 470 mg (0.99 mmol, 36%).

$^{13}$C-NMR: 24.67, 26.85, 26.95, 27.53, 28.96, 29.00, 29.53, 46.51, 47.39, 47.87, 56.70, 171.12, 172.29. MS: 475 (M+1). Anal. (C$_{26}$H$_{42}$N$_4$O$_4$.0.4 H$_2$O) C, H, N.

EXAMPLE 7

Succinic acid morpholine L-prolyl-pyrrolidine amide

The methyl ester group of 560 mg (2.0 mmol) succinic acid methyl ester L-prolyl-pyrrolidine amide was hydrolysed using 84 mg (2.0 mmol) LiOH.H$_2$O in 10 ml 20% water in methanol at rt. After 4 h the solvent was evaporated and the residue was dissolved in dichloromethane. The dichloromethane phase is dried and evaporated. The lithium salt of succinic acid mono-(L-prolyl-pyrrolidine)amide and 0.18 ml (2.0 mmol) morpholine were coupled according to procedure A. Yield of crude product 620 mg. The product was purified with a silica column using 20–25% methanol in ethyl acetate as eluent. Yield 330 mg (0.98 mmol, 49%).

$^{13}$C-NMR: 24.14, 24.78, 26.20, 27.68, 28.89, 29.33, 42.17, 45.84, 46.11, 46.45, 47.39, 58.04, 66.62, 66.86, 170.95, 171.01, 171.06. MS: 338 (M+1). Anal. (C$_{17}$H$_{27}$N$_3$O$_4$.0.3 H$_2$O) C, H, N.

EXAMPLE 8

Succinic acid di-(L-prolyl-morpholine)amide 430 mg (1.38 mmol) succinic acid di-L-proline amide and 0.24 ml (2.76 mmol) morpholine were coupled according to procedure A. Yield of crude product 500 mg. The product was purified with a silica column using methanol in ethyl acetate as eluent. Yield 210 mg (0.47 mmol, 34%).

$^{13}$C-NMR: 24.59, 28.83, 29.06, 42.40, 46.03, 47.04, 56.09, 66.57, 66.91, 170.62, 170.74. MS: 451 (M+1). Anal. (C$_{22}$H$_{34}$N$_4$O$_6$.0.3 H$_2$O) C, H, N.

EXAMPLE 9

Succinic acid hexamethyleneimine L-prolyl-pyrrolidine amide

The methyl ester group of 560 mg (2.0 mmol) succinic acid methyl ester L-prolyl-pyrrolidine amide was hydrolysed using 84 mg (2.0 mmol) LiOH.H$_2$O in 10 ml 20% water in methanol at rt. After 3 h the solvent was evaporated and the residue was dissolved in dichloromethane. The dichloromethane phase is dried and evaporated. The lithium salt of succinic acid mono-(L-prolyl-pyrrolidine)amide and 0.23 ml (2.0 mmol) hexamethyleneimine were coupled according to procedure A. Yield of crude product 540 mg. The product was purified with a silica column using 20% methanol in ethyl acetate as eluent. Yield 350 mg (1.00 mmol, 50%).

$^{13}$C-NMR: 24.13, 24.77, 26.22, 26.94, 27.12, 27.62, 28.00, 28.87, 28.99, 29.63, 45.92, 46.05, 46.27, 47.25, 47.74, 57.81, 170.76, 170.87, 171.60. MS: 350 (M+1). Anal. (C$_{19}$H$_{31}$N$_3$O$_3$.0.3 H$_2$O) C, H, N.

EXAMPLE 10

Terephthalic acid di-L-proline amide 2.03 g (10.0 mmol) terephthaloyl dichloride (dichloromethane) and 2.30 g (20.0 mmol) L-proline were coupled according to procedure C, using 1.92 g (48 mmol) NaOH and extracting the product with 50% ethanol in chloroform from the acidified aqueous phase. Yield 3.37 g (9.4 mmol, 94%).

Terephthalic acid di-(L-prolyl-pyrrolidine)amide 1.39 g (3.9 mmol) terephthalic acid di-L-proline amide and 0.64 ml (7.7 mmol) pyrrolidine were coupled according to procedure A. Yield of crude product 2.32 g. The product was purified with a silica column using 10–30% methanol in ethyl acetate as eluent. Yield 1.05 g (2.3 mmol, 58%).

$^{13}$C-NMR: 24.19, 25.57, 26.24, 28.98, 46.03, 46.41, 50.24, 58.15, 127.29, 138.00, 168.71, 170.35. MS: 467 (M+1). Anal. (C$_{26}$H$_{34}$N$_4$O$_4$.0.4 H$_2$O) C, H, N.

EXAMPLE 11

Isophthalic acid di-L-proline amide 2.03 g (10.0 mmol) isophthaloyl dichloride (dichloromethane) and 2.30 g (20.0 mmol) L-proline were coupled according to procedure C, using 1.92 g (48 mmol) NaOH and extracting the product with 50% ethanol in chloroform from the acidified aqueous phase.

Yield 3.61 g (10.0 mmol, 100%).

Isophthalic acid di-(L-prolyl-pyrrolidine)amide 1.39 g (3.9 mmol) isophthalic acid di-L-proline amide and 0.64 ml (7.7 mmol) pyrrolidine were coupled according to procedure A. Yield of crude product 2.23 g. The product was purified with a silica plate chromatotron using dichloromethane as eluent. Yield 280 mg (0.60 mmol, 15%).

$^{13}$C-NMR: 24.18, 25.57, 26.25, 28.99, 46.04, 46.42, 50.30, 58.23, 126.06, 128.24, 129.12, 136.60, 168.61, 170.34. MS: 467 (M+1). Anal. (C$_{26}$H$_{34}$N$_4$O$_4$.0.2 H$_2$O) C, H, N.

EXAMPLE 12

Isophthalic acid L-prolyl-2(S)-cyanopyrrolidine L-prolyl-pyrrolidine amide 980 mg (5.0 mmol) BOC-2(S)-cyanopyrrolidine was deprotected using 20 ml trifluoroacetic acid in 50 ml dichloromethane according to procedure J. 2.06 g (5.0 mmol)

isophthalic acid L-proline L-prolyl-pyrrolidine amide and the 2(S)-cyanopyrrolidine trifluoroacetic acid salt were coupled according to procedure A. Yield of crude product 2.14 g. The product was purified with a silica column using 2–5% methanol in dichloromethane as eluent. Yield 700 mg (1.4 mmol, 28%)

$^3$C-NMR: 23.01, 24.20, 25.43, 25.56, 26.25, 28.98, 29.80, 30.84, 46.05, 46.42, 46.50, 46.63, 50.27, 50.30, 58.03, 58.25, 118.63, 126.09, 128.36, 128.93, 129.29, 136.12, 136.77, 168.50, 168.83, 170.31, 171.13. MS: 492 (M+1). Anal. ($C_{27}H_{33}N_5O_4$.1.0 $H_2O$) C, H, N.

EXAMPLE 13

Isophthalic acid L-prolyl-benzylamine L-prolyl-pyrrolidine amide 650 mg (1.6 mmol) isophthalic acid L-proline L-prolyl-pyrrolidine amide and 0.17 ml (1.6 mmol) benzylamine were coupled according to procedure A. Yield of crude product 680 mg. The product was purified with a silica column using 10–13% methanol in ethyl acetate as eluent. Yield 480 mg (0.95 mmol, 60%).

$^{13}$C-NMR: 24.19, 25.43, 25.58, 26.23, 27.41, 28.97, 43.53, 46.07, 46.43, 50.30, 50.49, 58.28, 60.12, 125.98, 127.26, 127.50, 128.46, 128.64, 128.73, 129.20, 136.35, 136.80, 138.38, 168.40, 170.31, 170.49, 170.89. MS: 503 (M+1). Anal. ($C_{29}H_{34}N_4O_4$.0.3 $H_2O$) C, H, N.

EXAMPLE 14

Mono-BOC-piperazine

A solution of 2.18 g (10 mmol) di-tert-butyl dicarbonate in 20 ml dichloromethane was added slowly to a solution of 1.72 g (20 mmol) piperazine in dichloromethane at 0° C. The reaction mixture was left overnight at rt. The dichloromethane solution was washed with saturated $NaHCO_3$ aq and water. 60 ml diethyl ether was added and the organic phase was washed with water. The organic phase was dried with anhydrous $Na_2SO_4$ and evaporated. Yield of crude product 1.56 g. The product was purified with a silica column using methanol in dichloromethane as eluent. Yield 1.0 g (5.4 mmol, 54%).

Isophthalic acid L-prolyl-(Boc-piperazine) L-prolyl-pyrrolidine amide 580 mg (1.4 mmol) isophthalic acid L-proline L-prolyl-pyrrolidine amide and 260 mg (1.4 mmol) mono-BOC-piperazine were coupled according to procedure A. Yield of crude product 740 mg. The product was purified with a silica column using 20% methanol in ethyl acetate as eluent. Yield 490 mg (0.84 mmol, 60°%).

$^{13}$C-NMR: 24.19, 25.57, 26.24, 28.39, 28.98, 29.39, 30.80, 42.17, 45.72, 46.03, 46.40, 47.14, 50.18, 50.30, 56.35, 58.23, 60.34, 80.21, 126.06, 128.27, 128.99, 129.15, 136.46, 136.70, 154.62, 168.54, 168.65, 170.30, 170.58. MS: 582 (M+1). Anal. ($C_{31}H_{43}N_5O_6$.1.2 $H_2O$) C, H, N.

EXAMPLE 15

Isophthalic acid 2(S)-L-prolyl-piperazine L-prolyl-pyrrolidine amide 6 ml of HCl saturated ethyl acetate was added to 210 mg (0.36 mmol) isophthalic acid L-prolyl-(BOC-piperazine) L-prolyl-pyrrolidine amide. 27 ml ethyl acetate and 13 ml methanol had to be added in order to dissolve the starting material. The reaction mixture was left overnight at rt. The reaction mixture was evaporated. Yield of crude product 240 mg. The product was purified with a silica column using 25–100% methanol in ethyl acetate as eluent. The product was treated with HCl saturated ethyl acetate and dichloromethane to get it crystalline. The solvent was evaporated. Yield 150 mg (0.29 mmol, 80%). MS: 482 (M+1). Anal. ($C_{26}H_{35}N_5O_4$.HCl.1.8 $H_2O$) C, H, N.

EXAMPLE 16

Isophthalic acid (L-proline methyl ester) L-prolyl-pyrrolidine amide (See preparation of starting materials.)
MS: 428 (M+1). Anal. ($C_{23}H_{29}N_3O_5$.0.4 $H_2O$) C, H, N.

EXAMPLE 17

Isophthalic acid L-prolyl-hexamethyleneimine L-prolyl-pyrrolidine amide 1.15 g (2.8 mmol) isophthalic acid L-proline L-prolyl-pyrrolidine amide and 0.34 ml (3.0 mmol) hexamethyleneimine were coupled according to procedure A. Yield of crude product 1.45 g. The product was purified with a silica column using 20% methanol in ethyl acetate as eluent. Yield 1.02 g (2.06 mmol, 74%).

$^{13}$C-NMR: 24.20, 25.56, 26.25, 26.77, 26.93, 26.95, 27.58, 29.01, 29.13, 29.58, 46.03, 46.42, 46.53, 47.95, 50.29, 50.33, 56.83, 58.21, 126.04, 128.20, 129.02, 129.07, 136.68, 136.78, 168.54, 168.67, 170.36, 171.59. MS: 495 (M+1). Anal. ($C_{28}H_{38}N_4O_4$.0.9 $H_2O$) C, H, N.

EXAMPLE 18

Succinic acid mono-hexamethyleneimine amide 1.98 g (15 mmol) succinic acid mono-methyl ester and 1.7 ml (15 miol) hexamethyleneimine were coupled according to procedure A. Yield of crude product 2.85 g. The product was purified with a silica column using 30% petroleum ether in ethyl acetate as eluent. Yield 2.48 g (11.7 mmol, 78%). The methyl ester group of the product was hydrolysed using 540 mg (12.9 mmol) $LiOH.H_2O$ according to procedure H. Yield 2.34 g (11.7 mmol, 100%).

Succinic acid hexamethyleneimine L-proline amide 2.34 g (11.7 mmol) succinic acid mono-hexamethyleneimine amide and 1.9 g (11.7 mmol) proline methyl ester HCl salt were coupled according to procedure A. Yield of crude product 3.3 g. The product was purified with a silica column using 5% methanol in dichloromethane as eluent. Yield 2.22 g (7.15 mmol, 61%). The methyl ester group of the product was hydrolysed using 450 mg (10.7 mmol) $LiOH.H_2O$ according to procedure H. Yield 2.01 g (6.8 mmol, 95%).

Succinic acid hexamethyleneimine L-prolyl-2(S)-cyanopyrrolidine amide 1.3 g (6.8 mmol) BOC-2(S)-cyanopyrrolidine was deprotected using 27 ml trifluoroacetic acid in 70 ml dichloromethane according to procedure J. 2.01 g (6.8 mmol) succinic acid hexamethyleneimine L-proline amide and the 2(S)-cyanopyrrolidine trifluoroacetic acid salt were coupled according to procedure A. The product was purified with a silica column using 8–10% methanol in ethyl acetate as eluent. Yield 320 mg (0.85 mmol, 13%).

$^{13}$C-NMR: 24.83, 25.36, 26.92, 27.11, 27.59, 27.91, 28.73, 28.95, 29.50, 29.70, 46.04, 46.29, 46.49, 47.27, 47.71, 57.50, 118.60, 171.21, 171.33, 171.38. MS: 375 (M+1). Anal. ($C_{20}H_{30}N_4O_3 \cdot 0.2\ H_2O$) C, H, N.

EXAMPLE 19

Isophthalic acid mono-hexamethyleneimine amide 2.25 g (12.5 mmol) isophthalic acid mono-methyl ester and 1.41 ml (12.5 mmol) hexamethyleneimine were coupled according to procedure A. Yield of crude product 2.95 g. The product was purified with a silica column using 40% petroleum ether in ethyl acetate as eluent. Yield 2.02 g (7.7 mmol, 62%). The methyl ester group of the product was hydrolysed using 490 mg (11.7 mmol) $LiOH \cdot H_2O$ according to procedure H. Yield 1.89 g (7.6 mmol, 99%).

Isophthalic acid hexamethyleneimine L-proline amide 1.89 g (7.6 mmol) isophthalic acid mono-hexamethyleneimine amide and 1.27 g (7.6 mmol) proline methyl ester HCl salt were coupled according to procedure A. Yield of crude product 2.47 g. The product was purified with a silica column using 10% methanol in ethyl acetate as eluent. Yield 2.08 g (5.8 mmol, 76%). The methyl ester group of the product was hydrolysed using 370 mg (8.7 mmol) $LiOH \cdot H_2O$ according to procedure H. Yield 1.67 g (4.8 mmol, 83%).

Isophthalic acid hexamethyleneimine L-prolyl-2(S)-cyanopyrrolidine Amide 940 mg (4.8 mmol) BOC-2(S)-cyanopyrrolidine was deprotected using 19 ml trifluoroacetic acid in 50 ml dichloromethane according to procedure J. 1.67 g (4.8 mmol) isophthalic acid hexamethyleneimine L-proline amide and the 2(S)-cyanopyrrolidine trifluoroacetic acid salt were coupled according to procedure A. The product was purified with a silica column using 1.5–2.5% methanol in dichloromethane as eluent. Yield 920 mg (2.2 mmol, 45%).

$^{13}$C-NMR: 25.42, 25.71, 26.49, 27.23, 27.82, 28.98, 29.43, 29.78, 46.30, 46.46, 46.61, 49.84, 50.32, 58.02, 118.55, 125.32, 127.95, 128.35, 128.55, 136.24, 137.60, 168.82, 170.61, 171.12. MS: 423 (M+1). Anal. ($C_{24}H_{30}N_4O_3 \cdot 0.2\ H_2O$) C, H, N.

EXAMPLE 20

Isophthalic acid mono-pyrrolidine amide 2.25 g (12.5 mmol) isophthalic acid mono-methyl ester and 1.04 ml (12.5 mmol) pyrrolidine were coupled according to procedure A. Yield of crude product 2.4 g. The product was purified with a silica column using 30% petroleum ether in ethyl acetate as eluent. Yield 1.75 g (7.5 mmol, 60%). The methyl ester group of the product was hydrolysed using 470 mg (11.3 mmol) $LiOH \cdot H_2O$ according to procedure H. Yield 1.49 g (6.8 mmol, 91%).

Isophthalic acid L-proline pyrrolidine amide 1.49 g (6.8 mmol) isophthalic acid mono-pyrrolidine amide and 1.13 g (6.8 mmol) proline methyl ester HCl salt were coupled according to procedure A. Yield of crude product 2.19 g. The product was purified with a silica column using 10% methanol in ethyl acetate as eluent. Yield 1.83 g (5.5 mmol, 81%). The methyl ester group of the product was hydrolysed using 350 mg (8.3 mmol) $LiOH \cdot H_2O$ according to procedure H. Yield 1.58 g (5.0 mmol, 91%).

Isophthalic acid L-prolyl-2(S)-cyanopyrrolidine pyrrolidine amide 980 mg (5.0 mmol) BOC-2(S)-cyanopyrrolidine was deprotected using 20 ml trifluoroacetic acid in 50 ml dichloromethane according to procedure J. 1.58 g (5.0 mmol) isophthalic acid L-proline pyrrolidine amide and the 2(S)-cyanopyrrolidine trifluoroacetic acid salt were coupled according to procedure A. The product was purified with a silica column using 1.5–3% methanol in dichloromethane as eluent. Yield 730 mg (1.9 mmol, 37%).

$^{13}$C-NMR: 24.45, 25.41, 25.69, 26.36, 28.98, 29.77, 46.24, 46.47, 46.62, 49.57, 50.32, 58.02, 118.56, 125.82, 128.51, 128.58, 128.95, 136.10, 137.53, 168.79, 168.83, 171.14. MS: 395 (M+1). Anal. ($C_{22}H_{26}N_4O_3 \cdot 0.3\ H_2O$) C, H, N.

EXAMPLE 21

Succinic acid di-(L-prolyl-2(S)-cyanopyrrolidine)amide 860 mg (4.4 mmol) BOC-2(S)-cyanopyrrolidine was deprotected using 18 ml trifluoroacetic acid in 50 ml dichloromethane according to procedure J. 700 mg (2.2 mmol) succinic acid di-(L-proline)amide and the 2(S)-cyanopyrrolidine trifluoroacetic acid salt were coupled according to procedure A. Yield of crude product 1.00 g. The product was purified with a silica column using 2.5–5% methanol in ethyl acetate as eluent. Yield 100 mg (0.21 mmol, 10%).

$^{13}$C-NMR: 24.73, 25.36, 28.68, 28.79, 29.70, 46.23, 46.52, 47.16, 57.53, 118.54, 170.75, 171.21. MS: 469 (M+1)

EXAMPLE 22

Isophthalic acid L-prolyl-2(S)-(acetoxyacetyl)pyrrolidine L-prolyl-pyrrolidine amide 1.4 g (5.0 mmol) BOC-2(S)-(acetoxyacetyl)pyrrolidine was deprotected using 20 ml trifluoroacetic acid in 50 ml dichloromethane according to procedure J. 2.06 g (5.0 mmol) isophthalic acid L-proline L-prolyl-pyrrolidine amide and the 2(S)-(acetoxyacetyl)pyrrolidine trifluoroacetic acid salt were coupled according to procedure A. Yield of crude product 1.51 g. The product was purified with a silica column using 3–5% methanol in dichloromethane as eluent. Yield 1.0 g (1.76 mmol, 35%)

Isophthalic acid L-prolyl-2(S)-(hydroxyacetyl)pyrrolidine L-prolyl-pyrrolidine amide 1.0 g (1.76 mmol) isophthalic acid L-prolyl-2(S)-acetoxyacetyl)pyrrolidine L-prolyl-pyrrolidine amide was hydrolysed according to procedure I. Yield of crude product 900 mg. The product was purified with a silica column using 5% methanol dichloromethane as eluent. Yield 470 mg (0.44 mmol, 51%) $^{13}$C-NMR: 24.19, 25.39, 25.52, 25.56, 26.24, 28.26, 28.75, 28.97, 46.03, 46.40, 47.18, 50.26, 50.29, 58.03, 58.21, 61.11, 67.14, 126.08, 128.30, 128.98, 129.22, 136.24, 136.67, 168.52, 168.73, 170.27, 170.89. MS: 525 (M+1). Anal. ($C_{28}H_{36}N_4O_6 \cdot 0.4\ H_2O$) C, H, N.

EXAMPLE 23

Phthalic acid di-(L-proline methyl ester)amide 1.04 g (3.8 mmol) phthalic acid mono-(L-proline methyl ester)amide and 0.63 g (3.8 mmol) L-proline methyl ester HCl salt were coupled according to procedure A. Yield 1.20 g (3.1 mmol, 81%).

Phthalic acid di-L-proline amide

The methyl ester group of 1.20 g (3.1 mmol) phthalic acid di-(L-proline methyl ester) amide was hydrolysed using 400 mg (9.6 mmol) $LiOH \cdot H_2O$ according to procedure H. Yield 0.99 g (3.1 mmol, 94%).

Phthalic acid di-(L-prolyl-pyrrolidine)amide 740 mg (2.1 mmol) phthalic acid di-L-proline amide and 0.4 ml (4.6 mmol) pyrrolidine were coupled according to procedure A. Yield of crude product 880 mg. The product was purified with a silica plate chromatotron using 5% methanol in dichloromethane as eluent. Yield 320 mg (0.69 mmol, 33%).

$^{13}$C-NMR: 23.30, 23.97, 24.13, 25.19, 25.89, 26.23, 29.09, 30.54, 45.64, 45.79, 45.99, 46.21, 46.86, 49.93, 57.51, 59.19, 126.89, 127.37, 128.26, 128.87, 134.78, 135.60, 168.75, 168.78, 170.45, 170.80. MS: 467 (M+1). Anal. ($C_{26}H_{34}N_4O_4$.0.7 $H_2O$) C, H, N.

EXAMPLE 24

Isophthalic acid 2(S)-cyclopentanecarbonyl)pyrrolidine L-prolyl-pyrrolidine amide 400 mg (1.5 mmol) BOC-2(S)-(cyclopentanecarbonyl)pyrrolidine was deprotected using 6 ml trifluoroacetic acid in 50 ml dichloromethane according to procedure J. 490 mg (1.5 mmol) isophthalic acid mono-L-prolyl-pyrrolidine amide and the 2(S)-cyclopentanecarbonyl)pyrrolidine trifluoroacetic acid salt were coupled according to procedure A. Yield of crude product 640 mg. The product was purified with a silica plate chromatotron using 5% methanol in dichloromethane as eluent. Yield 460 mg (0.99 mmol, 66%).

$^{13}$C-NMR: 24.19, 25.49, 25.59, 26.06, 26.18, 26.24, 28.61, 28.65, 28.99, 29.57, 46.03, 46.39, 49.16, 50.31, 58.23, 60.39, 64.44, 125.96, 128.35, 129.03, 129.19, 136.40, 136.61, 168.54, 168.62, 170.28, 193.47. MS: 466 (M+1). Anal. ($C_{27}H_{35}N_3O_4$.0.2 $H_2O$) C, H, N.

EXAMPLE 25

Isophthalic acid 2(S)-acetylpyrrolidine L-prolyl-pyrrolidine amide 900 mg (4.2 mmol) BOC-2(S)-acetylpyrrolidine was deprotected using 8.4 ml trifluoroacetic acid in 50 ml dichloromethane according to procedure J. 1.33 mg (4.2 mmol) isophthalic acid mono-L-prolyl-pyrrolidine amide and the 2(S)-acetylpyrrolidine trifluoroacetic acid salt were coupled according to procedure A. Yield of crude product 1.61 g. The product was purified with a silica column using 10–20% methanol in ethyl acetate as eluent. Yield 1.00 g (2.4 mmol, 58%).

$^{13}$C-NMR: 24.18, 25.39, 25.60, 26.23, 27.06, 28.21, 28.98, 46.04, 46.40, 50.24, 50.33, 58.26, 65.43, 125.99, 128.42, 129.01, 129.25, 136.21, 136.63, 168.46, 168.93, 170.28, 206.35. MS: 412 (M+1). Anal. ($C_{23}H_{29}N_3O_4$.0.7 $H_2O$) C, H, N.

EXAMPLE 26

Phthalic acid L-prolyl-2(S)-cyanopyrrolidine pyrrolidine amide 980 mg (5.0 mmol) BOC-2(S)-cyanopyrrolidine was deprotected using 10 ml trifluoroacetic acid in 50 ml dichloromethane according to procedure J. 1.58 g (5.0 mmol) phthalic acid L-proline pyrrolidine amide and the 2(S)-cyanopyrrolidine trifluoroacetic acid salt were coupled according to procedure A. Yield of crude product 2.08 g. The product was purified with a silica plate chromatotron using 2% methanol in dichloromethane as eluent. Yield 250 mg (0.63 mmol, 13%)

$^{13}$C-NMR: 24.55, 25.30, 25.38, 26.03, 29.15, 29.74, 45.72, 46.26, 46.59, 48.96, 49.74, 57.38, 118.58, 126.52, 127.19, 129.07, 135.42, 135.75, 168.63, 168.92, 171.04. MS: 395 (M+1). Anal. ($C_{22}H_{26}N_4O_3$.0.3 $H_2O$) C, H, N.

EXAMPLE 27

Phthalic acid L-proline L-prolyl-pyrrolidine amide 1.34 g (5.0 mmol) BOC-L-prolyl-pyrrolidine was deprotected using 20 ml trifluoroacetic acid in 50 ml dichloromethane according to procedure J. 1.39 g (5.0 mmol) phthalic acid mono-(L-proline methyl ester)amide and the L-prolyl-pyrrolidine trifluoroacetic acid salt were coupled according to procedure A. Yield of crude product 1.66 g. The product was purified with a silica column using 7–10% methanol in ethyl acetate as eluent. Yield 950 mg (2.2 mmol, 44%). The methyl ester group of the product was hydrolysed using 140 mg (3.3 mmol) LiOH.$H_2O$ according to procedure H. Yield 720 mg (1.74 mmol, 78%).

Phthalic acid L-prolyl-2(S)-cyanopyrrolidine L-prolyl-pyrrolidine amide 340 mg (1.74 mmol) BOC-2(S)-cyanopyrrolidine was deprotected using 3.5 ml trifluoroacetic acid in 20 ml dichloromethane according to procedure J. 0.72 g (1.74 mmol) phthalic acid L-proline L-prolyl-pyrrolidine amide and the 2(S)-cyanopyrrolidine trifluoroacetic acid salt were coupled according to procedure A. Yield of crude product 730 mg. The product was purified with a silica plate chromatotron using 3% methanol in dichloromethane as eluent. Yield 300 mg (0.61 mmol, 35%)

$^{13}$C-NMR: 23.28, 23.94, 24.10, 24.95, 25.22, 25.26, 25.36, 25.86, 26.20, 27.19, 29.02, 29.05, 29.55, 29.71, 30.52, 45.68, 45.70, 45.79, 46.04, 46.16, 46.22, 46.61, 46.96, 46.99, 49.85, 49.97, 57.28, 57.59, 58.72, 159.17, 117.94, 118.53, 127.00, 127.15, 127.50, 128.18, 128.36, 128.46, 129.07, 129.11, 134.57, 134.77, 135.25, 135.33, 168.52, 168.60, 168.69, 169.00, 170.37, 170.57, 171.13, 171.43. MS: 492 (M+1)

EXAMPLE 28

Succinic acid mono-pyrrolidine amide 1.98 g (15 mmol) succinic acid monomethyl ester and 1.3 ml (15 mmol) pyrrolidine were coupled according to procedure A. Yield of crude product 2.32 g. The product was purified with a silica column using ethyl acetate as eluent. Yield 1.75 g (9.45 mmol, 63%). The methyl ester group of the product was hydrolysed using 440 mg (10.4 mmol) LiOH.$H_2O$ according to procedure H. Yield 1.37 g (8.00 mmol, 85%).

Succinic acid L-proline pyrrolidine amide 1.37 g (8.0 mmol) succinic acid mono-pyrrolidine amide and 1.3 g (8.0 mmol) proline methyl ester HCl salt were coupled according to procedure A. Yield of crude product 1.92 g. The product was purified with a silica column using 5% methanol in dichloromethane as eluent. Yield 1.45 g (5.1 mmol, 64%). The methyl ester group of the product was hydrolysed using 320 mg (7.65 mmol) LiOH.$H_2O$ according to procedure H. Yield 1.32 g (4.9 mmol, 96%).

Succinic acid L-prolyl-2(S)-cyanopyrrolidine pyrrolidine amide 960 mg (4.9 mmol) BOC-2(S)-cyanopyrrolidine was deprotected using 20 ml trifluoroacetic acid in 50 ml dichloromethane according to procedure J. 1.32 g (4.9 mmol)

succinic acid L-proline pyrrolidine amide and the 2(S)-cyanopyrrolidine trifluoroacetic acid salt were coupled according to procedure A. The product was purified with a silica column using 10% methanol in ethyl acetate as eluent. Yield 170 mg (0.49 mmol, 10%).

$^{13}$C-NMR: 24.39, 24.82, 25.37, 26.04, 28.73, 29.05, 29.27, 29.70, 45.70, 46.28, 46.42, 46.50, 47.30, 57.52, 118.58, 170.26, 171.15, 171.36. MS: 347 (M+1). Anal. ($C_{18}H_{26}N_4O_3$.0.2 $H_2O$) C, H, N.

EXAMPLE 29

Phthalic acid L-prolyl-pyrrolidine pyrrolidine amide 900 mg (2.8 mmol) phthalic acid L-proline pyrrolidine amide 0.26 ml (3.1 mmol) pyrrolidine were coupled according to procedure A. Yield of crude product 1.31 g. The product was purified with a silica column using 10% methanol in ethyl acetate as eluent. Yield 860 mg (2.3 mmol, 83%)

$^{13}$C-NMR: 23.33, 23.99, 24.16, 24.54, 25.22, 25.91, 25.99, 26.23, 29.18, 30.53, 45.64, 45.64, 45.69, 45.74, 45.97, 46.25, 46.80, 48.79, 48.91, 49.80, 57.61, 59.37, 125.70, 126.39, 127.38, 127.45, 128.54, 128.65, 128.89, 128.91, 135.15, 135.61, 135.73, 135.85, 168.63, 168.70, 168.82, 168.96, 170.34, 171.09. MS: 370 (M+1). Anal. ($C_{21}H_{27}N_3O_3$.0.3 $H_2O$) C, H, N.

EXAMPLE 30

Isophthalic acid 2(S)-(cyclopentanecarbonyl)pyrrolidine (L-proline methyl ester) amide (See preparation of starting materials.)

$^{13}$C-NMR: 25.35, 25.37, 25.49, 26.05, 26.18, 28.61, 28.63, 29.41, 29.59, 49.27, 49.29, 49.97, 50.31, 50.70, 52.31, 59.23, 64.42, 125.97, 128.45, 128.51, 128.98, 129.03, 129.07, 136.35, 136.38, 136.47, 136.51, 168.54, 168.91, 172.60, 210.89. MS: 427 (M+1). Anal. ($C_{24}H_{30}N_2O_5$) C, H, N.

EXAMPLE 31

Isophthalic acid 2(S)-acetylpyrrolidine L-prolyl-2(S)-(acetoxyacetyl)pyrrolidine amide 0.81 g (3.0 mmol) BOC-2(S)-(acetoxyacetyl)pyrrolidine was deprotected using 6 ml trifluoroacetic acid in 30 ml dichloromethane according to procedure J. 1.06 g (3.0 mmol) isophthalic acid 2(S)-acetylpyrrolidine L-proline amide and the 2(S)-(acetoxyacetyl)pyrrolidine trifluoroacetic acid salt were coupled according to procedure A. Yield of crude product 750 mg. The product was purified with a silica column using 10% methanol in ethyl acetate as eluent. Yield 340 mg (0.66 mmol, 22%).

Isophthalic acid 2(S)-acetylpyrrolidine L-prolyl-2(S)-(hydroxyacetyl)pyrrolidine amide 340 mg (0.66 mmol) isophthalic acid 2(S)-acetylpyrrolidine L-prolyl-2(S)=(acetoxyacetyl) pyrrolidine amide was hydrolysed according to procedure I. Yield of crude product 268 mg. The product was purified with a silica column using 10% methanol in ethyl acetate as eluent. Yield 209 mg (0.45 mmol, 67%)

$^{13}$C-NMR: 25.32, 25.36, 25.56, 25.59, 27.13, 27.18, 28.19, 28.26, 28.75, 47.19, 50.18, 50.20, 50.31, 50.32, 50.74, 58.12, 61.18, 65.33, 65.39, 67.11, 125.98, 126.03, 128.46, 128.56, 129.13, 129.14, 129.16, 136.19, 136.26, 136.30, 168.62, 168.63, 168.81, 168.84, 170.90, 170.92, 206.30, 206.33, 208.94. MS: 470 (M+1). Anal. ($C_{25}H_{31}N_3O$) C, H, N.

EXAMPLE 32

Isophthalic acid di-glycine amide 2.0 g (10.0 mmol) isophthaloyl dichloride (diethyl ether) and 1.5 g (20.0 mmol) glycine were coupled according to procedure C, using 40.0 mmol NaOH and extracting the product with 25% ethanol in dichloromethane from the acidified aqueous phase. Yield 1.67 g (6.0 mmol, 60%).

Isophthalic acid di-(glycyl-pyrrolidine)amide 1.67 g (6.0 mmol) isophthalic acid di-glycine amide and 1.1 ml (13.2 mmol) pyrrolidine were coupled according to procedure A. Yield of crude product 1.79 g. The product was recrystallized from dichloromethane in hexane. Yield 800 mg (2.1 mmol, 35%).

$^{13}$C-NMR: 24.11, 25.92, 42.55, 45.53, 46.00, 125.89, 128.71, 130.15, 134.33, 166.44, 166.54. MS: 387 (M+1)

EXAMPLE 33

Isopbthalic acid di-(2(S)-acetylpyrrolidine)amide 800 mg (4.0 mmol) BOC-2(S)-acetylpyrrolidine was deprotected using 8 ml trifluoroacetic acid in 40 ml dichloromethane according to procedure J. The 2(S)-acetylpyrrolidine trifluoroacetic acid salt (dichloromethane) was added to 410 mg (2.0 mmol) isophthaloyl chloride (diethyl ether) according to procedure D. The crude product was purified by a silica column using 2–5% methanol ethyl acetate as eluent. Yield 420 mg (1.2 mmol, 59%).

$^{13}$C-NMR: 25.38, 27.20, 28.20, 50.22, 65.38, 126.05, 128.49, 128.56, 129.07, 136.29, 136.35, 168.75, 206.25. MS: 357 (M+1)

EXAMPLE 34

Isophthalic acid 2(S)-acetylpyrrolidine L-prolyl-2(S)-cyanopyrrolidine amide 452 mg (2.3 mmol) BOC-2(S)-cyanopyrrolidine was deprotected using 5 ml trifluoroacetic acid in 30 ml dichloromethane according to procedure J. 810 mg (2.3 mmol) isophthalic acid 2(S)-acetylpyrrolidine L-proline amide and the 2(S)-cyanopyrrolidine trifluoroacetic acid salt were coupled according to procedure A. The product was purified with a silica column using 5% methanol in ethyl acetate as eluent. Yield 230 mg (0.53 mmol, 23%).

$^{13}$C-NMR: 25.31, 25.38, 25.42, 25.69, 27.15, 27.23, 28.18, 28.98, 29.78, 46.48, 46.62, 46.63, 50.17, 50.20, 50.30, 50.32, 58.07, 65.32, 65.39, 118.55, 125.93, 126.00, 128.51, 128.60, 129.05, 129.09, 129.17, 129.20, 136.12, 136.20, 136.39, 136.40, 168.69, 168.74, 168.77, 171.09, 171.10, 206.21, 206.24. MS: 437 (M+1). Anal. ($C_{24}H_{28}N_4O_4$.0.2 $H_2O$) C, H, N.

EXAMPLE 35

Isophthalic acid 2(S)-(cyclopentanecarbonyl)pyrrolidine L-prolyl-2(S)-cyanopyrrolidine amide 0.42 g (2.1 mmol) BOC-2(S)-cyanopyrrolidine was deprotected using 4.2 ml trifluoroacetic acid in 30 ml dichloromethane according to procedure J. 0.87 g (2.1 mmol) isophthalic acid 2(S)-(cyclopentanecarbonyl)pyrrolidine L-proline amide and the 2(S)-cyanopyrrolidine trifluoroacetic acid salt were coupled according to procedure A. Yield of crude product 1.05 mg. The product was purified with a silica column using 10% methanol in ethyl acetate as eluent. Yield 230 mg (0.47 mmol, 22%).

$^{13}$C-NMR: 25.42, 25.67, 26.04, 26.18, 28.59, 28.64, 28.98, 29.58, 29.79, 46.48, 46.61, 49.24, 49.27, 50.25, 50.28, 50.29, 50.31, 58.02, 64.33, 64.41, 118.57, 125.87, 125.97, 128.44, 128.55, 128.93, 129.00, 129.14, 129.21, 136.09, 136.17, 136.59, 168.44, 168.74, 171.09, 171.11, 210.77, 210.84. MS: 491 (M+1). Anal. ($C_{28}H_{34}N_4O_4 \cdot 0.1$ $H_2O$) C, H, N.

EXAMPLE 36

Isophthalic acid 2(S)-(cyclopentanecarbonyl)pyrrolidine L-prolyl-2(S)-(acetoxyacetyl) pyrrolidine amide 0.63 g (2.3 mmol) BOC-2(S)-acetoxyacetyl)pyrrolidine was deprotected using 5 ml trifluoroacetic acid in 30 ml dichloromethane according to procedure J. 0.90 g (2.2 mmol) isophthalic acid 2(S)-(cyclopentanecarbonyl)pyrrolidine L-proline amide and the 2(S)-(acetoxyacetyl)pyrrolidine trifluoroacetic acid salt were coupled according to procedure A. Yield of crude product 930 mg. The product was purified with a silica column using 10% methanol in ethyl acetate as eluent. Yield 370 mg (0.65 mmol, 30%).

Isophthalic acid 2(S)-cyclopentanecarbonyl)pyrrolidine L-prolyl-2(S)-(hydroxyacetyl)pyrrolidine amide 370 mg (0.65 mmol) isophthalic acid 2(S)-(cyclopentanecarbonyl)pyrrolidine L-prolyl-2(S)-(acetoxyacetyl)pyrrolidine amide was hydrolysed according to procedure I. Yield of crude product 330 mg. The product was purified with a silica column using 5% methanol dichloromethane as eluent. Yield 230 mg (0.44 mmol, 68%).

$^{13}$C-NMR: 25.40, 26.05, 26.19, 28, 27, 28.60, 28.65, 28.77, 29.58, 47.20, 49.26, 50.27, 50.30, 58.07, 61.15, 64.41, 67.12, 126.00, 128.39, 129.02, 129.10, 136.31, 136.54, 168.52, 168.69, 170.96, 208.94, 210.81. MS: 524 (M+1). Anal. ($C_{29}H_{37}N_3O_6 \cdot 0.4 H_2O$) C, H, N.

EXAMPLE 37

Isophthalic acid mono-2(S)-benzoylpyrrolidine amide 1.96 g (7.1 mmol) BOC-2(S)-benzoylpyrrolidine was deprotected using 14.2 ml trifluoroacetic acid in 70 ml dichloromethane according to procedure J. 1.28 g (7.1 mmol) isophthalic acid monomethyl ester and 2(S)-benzoylpyrrolidine trifluoroacetic acid salt were coupled according to procedure A. Yield of crude product 2.62 g. The product was purified with a silica column using 33–50% ethyl acetate in petroleum ether as eluent. Yield 1.1 g (3.3 mmol, 46%). The methyl ester group of the product was hydrolysed using 210 mg (4.95 mmol) LiOH.H$_2$O according to procedure H. 110 ml 15% water in methanol had to be used because of low solubility. Further 210 mg (4.95 mmol) LiOH.H$_2$O and 10 ml water had to be added after 24 h and the reaction was kept overnight. Yield 990 mg (3.1 mmol, 94%).

Isophthalic acid L-proline 2(S)-benzoylpyrrolidine amide 0.99 g (3.1 mmol) isophthalic acid mono-2(S)-benzoylpyrrolidine amide and 0.56 g (3.4 mmol) proline methyl ester HCl salt were coupled according to procedure A. Yield of crude product 1.37 g. The methyl ester group of the product was hydrolysed using 210 mg (4.8 mmol) LiOH.H$_2$O according to procedure H. Yield 1.27 g (3.0 mmol, 99%).

Isophthalic acid 2(S)-benzoylpyrrolidine L-prolyl-2(S)-cyanopyrrolidine amide 590 mg (3.0 mmol) BOC-2(S)-cyanopyrrolidine was deprotected using 6 ml trifluoroacetic acid in 30 ml dichloromethane according to procedure J. 1.27 g (3.0 mmol) isophthalic acid L-proline 2(S)-benzoylpyrrolidine amide and the 2(S)-cyanopyrrolidine trifluoroacetic acid salt were coupled according to procedure A. Yield of crude product 1.45 mg. The product was purified with a silica column using 10% methanol in ethyl acetate as eluent. Yield 420 mg (0.84 mmol, 28%)

$^{13}$C-NMR: 25.39, 25.42, 25.65, 25.68, 28.98, 29.49, 29.79, 46.49, 46.63, 50.14, 50.31, 58.08, 61.51, 118.60, 125.93, 126.04, 128.46, 128.51, 128.58, 128.72, 128.81, 128.86, 128.94, 128.99, 129.23, 129.28, 133.38, 133.58, 135.28, 136.07, 136.12, 136.60, 136.63, 168.41, 168.78, 168.80, 171.12, 171.15, 197.35, 197.44. MS: 499 (M+1). Anal. ($C_{29}H_{30}N_4O_4 \cdot 0.7 H_2O$) C, H, N.

EXAMPLE 38

BOC-2(S)-isobutanoylpyrrolidine 30.1 ml (60.2 mmol) 2 M isopropylmagnesium chloride (diethyl ether) and 4.0 g (20.1 mmol) BOC-L-prolinal were allowed to react at −80° C. for 30 min according to procedure F. Yield of the crude product 4.31 g. The product was purified with a silica column using 16% ethyl acetate in petroleum ether as eluent. Yield 1.84 g (7.6 mmol, 38%). The product was oxidized to the corresponding ketone according to procedure G. Yield of crude product 1.59 g. The product was purified with a silica column using 16% ethyl acetate in petroleum ether as eluent. Yield 1.15 g (4.8 mmol, 63%).

Isophthalic acid mono-2(S)-isobutanoylpyrrolidine amide 1.74 g (7.2 mmol) BOC-2(S)-isobutanoylpyrrolidine was deprotected using 15 ml trifluoroacetic acid in 70 ml dichloromethane according to procedure J. 1.3 g (7.2 mmol) isophthalic acid monomethyl ester and 2(S)-isobutanoylpyrrolidine trifluoroacetic acid salt were coupled according to procedure A. Yield of crude product 2.35 g. The product was purified with a silica column using 33–40% ethyl acetate in petroleum ether as eluent. Yield 1.35 g (4.5 mmol, 62%). The methyl ester group of the product was hydrolysed using 284 mg (6.8 mmol) LiOH.H$_2$O according to procedure H. Yield 1.19 g (4.1 mmol, 91%).

Isophthalic acid 2(S)-isobutanoylpyrrolidine L-proline amide 1.19 g (4.1 mmol) isophthalic acid mono-2(S)-isobutanoylpyrrolidine amide and 0.75 g (4.5 nmol) proline methyl ester HCl salt were coupled according to procedure A Yield of crude product 1.7 g. The methyl ester group of the product was hydrolysed using 265 mg (6.3 mmol) LiOH.H$_2$O according to procedure H. Yield 1.55 g (4.0 mmol, 98%).

Isophthalic acid 2(S)-isobutanoylpyrrolidine L-prolyl-2(S)-cyanopyrrolidine amide 787 mg (4.0 mmol) BOC-2(S)-cyanopyrrolidine was deprotected using 8 ml trifluoroacetic acid in 30 ml dichloromethane according to procedure J. 1.55 g (4.0 mmol) isophthalic acid L-proline 2(S)-isobutanoylpyrrolidine amide and the 2(S)-cyanopyrrolidine trifluoroacetic acid salt were coupled according to procedure A. Yield of crude product 1.52 g. The product was purified with a silica column using 5–10% methanol in ethyl acetate as eluent. Yield 300 mg (0.65 mmol, 16%).

$^{13}$C-NMR: 18.09, 18.49, 25.42, 25.46, 25.66, 28.79, 28.98, 29.78, 39.15, 46.48, 46.62, 50.20, 50.30, 58.04, 63.35, 118.58, 125.86, 128.56, 128.94, 129.13, 136.09, 136.51, 168.37, 168.75, 171.12, 212.26. MS: 465 (M+1). Anal. ($C_{26}H_{32}N_4O_4$·0.5 $H_2O$) C, H, N.

EXAMPLE 39

Isophthalic acid L-prolyl-L-prolinol L-prolyl-pyrrolidine amide 770 mg (1.8 mmol) isophthalic acid L-proline L-prolyl-pyrrolidine amide and 0.18 g (1.8 mmol) L-prolinol were coupled according to procedure A. Yield of crude product 370 mg (0.75 mmol, 41%)

Isophthalic acid L-prolyl-pyrrolidine L-prolyl-L-prolinal amide 370 mg (0.75 mmol) isophthalic acid L-prolyl-pyrrolidine L-prolyl-L-prolinol amide was oxidized to the corresponding aldehyde according to procedure G. Yield of crude product 300 mg. The product was purified with a silica column using 33% methanol in ethyl acetate as eluent. Yield 170 mg (0.34 mmol, 46%).

$^{13}$C-NMR: 24.19, 25.04, 25.52, 25.55, 25.55, 26.24, 28.98, 29.26, 46.04, 46.40, 47.08, 50.27, 50.29, 58.05, 58.24, 64.89, 126.04, 128.30, 128.99, 129.19, 136.34, 136.69, 168.53, 168.73, 170.29, 171.38, 198.92. MS: 495 (M+1). Anal. ($C_{27}H_{34}N_4O_5$·2.2 $H_2O$) C, H, N.

EXAMPLE 40

Isophthalic acid mono-L-alanyl-pyrrolidine amide 2.42 g (10 mmol) BOC-L-alanyl-pyrrolidine was deprotected using 20 ml trifluoroacetic acid in 100 ml dichloromethane according to procedure J. 1.80 g (10 mmol) isophthalic acid monomethyl ester and the L-alanyl-pyrrolidine trifluoroacetic acid salt were coupled according to procedure A. Yield of crude product 3.62 g. The methyl ester group of the product was hydrolysed using 630 mg (15 mmol) LiOH·$H_2O$ according to procedure H. Yield 1.91 g (6.6 mmol, 66%).

Isopnthalic acid L-proline L-alanyl-pyrrolidine amide 1.91 g (6.6 mmol) isophthalic acid mono-L-alanyl-pyrrolidine amide and 1.09 g (6.6 mmol) L-proline methyl ester HCl salt were coupled according to procedure A. Yield of crude product 2.56 g. The product was purified by a silica column using 10% methanol in ethyl acetate as eluent. Yield 950 mg (2.4 mmol, 36%). The methyl ester group of the product was hydrolysed using 150 mg (3.6 mmol) LiOH·$H_2O$ according to procedure H. Yield 760 mg (2.0 mmol, 83%).

Isophthalic acid L-prolyl-pyrrolidine L-alanyl-L-pyrrolidine amide 760 mg (2.0 mmol) isophthalic acid L-proline L-alanyl-pyrrolidine amide and 0.18 ml (2.2 mmol) pyrrolidine were coupled according to procedure A. Yield of crude product 720 mg. The product was purified by a silica column using 1025% methanol in ethyl acetate as eluent. Yield 680 g (1.54 mmol, 79%).

$^{13}$C-NMR: 18.40, 24.15, 24.20, 25.57, 26.09, 26.25, 29.03, 46.08, 46.13, 46.46, 47.42, 50.31, 58.24, 125.95, 128.58, 128.78, 130.45, 134.31, 136.94, 165.75, 168.55, 170.41, 170.83. MS: 441 (M+1). Anal. ($C_{24}H_{32}N_4O_4$·0.3 $H_2O$) C, H, N.

EXAMPLE 41

Isophthalic acid di-(2(S)-(cyclopentanecarbonyl)pyrrolidine)amide 610 mg (2.28 mmol) BOC-2(S)-(cyclopentanecarbonyl) pyrrolidine was deprotected using 4.6 ml trifluoroacetic acid in 30 ml dichloromethane according to procedure J. The 2(S)-(cyclopentanecarbonyl) pyrrolidine trifluoroacetic acid salt (dichloromethane) was added to 230 mg (1.14 mmol) isophthaloyl chloride (diethyl ether) according to procedure D. Yield of crude product 500 mg. The product was purified by a silica column using ethyl acetate as eluent. Yield 454 mg (0.98 mmol, 86%).

$^{13}$C-NMR: 26.05, 26.05, 26.19, 28.63, 28.65, 29.59, 49.27, 50.31, 64.42, 125.90, 128.43, 129.02, 136.54, 168.57, 210.86. MS: 465 (M+1). Anal. ($C_{28}H_{36}N_2O_4$·0.2 $H_2O$) C, H, N.

EXAMPLE 42

3,3-Dimethyl glutaric acid dichloride 4.9 ml (68 mmol) thionyl chloride was added to 3.3 g (20.6 mmol) 3,3-dimethyl glutaric acid at rt. The reaction mixture was stirred at rt for 2 d. The excess of thionyl chloride was evaporated and the product was vacuum distilled at 20 mbar and 115° C. Yield 1.65 g (8.37 mmol, 41%).

3,3-Dimethyl glutaric acid di-L-proline amide 1.65 g (8.37 mmol) 3,3-dimethyl glutaric acid dichloride (diethyl ether) 2.12 g (18.4 mmol) L-proline were coupled according to procedure C, using 2.0 g (50 mmol) NaOH and extracting the product with 50% ethanol in chloroform from the acidified aqueous phase. Yield 2.52 g (7.1 mmol, 85%).

3,3-Dimethyl glutaric acid di-(L-prolyl-pyrrolidine)amide 2.5 g (7.0 mmol) 3,3-dimethyl glutaric acid di-L-proline amide 1.3 ml (15.4 mmol) pyrrolidine were coupled according to procedure A. Yield of crude product 2.87 g. The product was purified by a silica column using 10–40% methanol in ethyl acetate as eluent. Yield 1.02 g (2.2 mmol, 32%).

$^{13}$C-NMR: 24.13, 24.94, 26.22, 28.39, 28.86, 34.30, 44.32, 45.91, 46.20, 48.12, 57.72, 170.74, 170.78. MS: 461 (M+1). Anal. ($C_{25}H_{40}N_4O_4$·1.0 $H_2O$) C, H, N.

EXAMPLE 43

Isophthalic acid 2(S)-(cyclohexanecarbonyl)pyrrolidine L-prolyl-2(S)-cyanopyrrolidine amide 0.36 g (1.84 mmol) BOC-2(S)-cyanopyrrolidine was deprotected using 5 ml trifluoroacetic acid in 30 ml dichloromethane according to procedure J. 785 mg (1.84 mmol) isophthalic acid L-proline 2(S)-(cyclohexanecarbonyl)pyrrolidine amide and the 2(S)-cyanopyrrolidine trifluoroacetic acid salt were coupled according to procedure A. Yield of crude product 920 mg. The product was purified with a silica column using ethyl acetate as eluent. Yield 255 mg (0.51 mmol, 27%).

$^{13}$C-NMR: 25.42, 25.66, 25.68, 25.71, 25.88, 28.33, 28.66, 28.72, 28.98, 29.79, 46.49, 46.63, 49.15, 50.23, 50.30, 58.05, 63.39, 63.46, 118.58, 125.88, 125.98, 128.45, 128.55, 128.94, 129.00, 129.14, 129.20, 136.09, 136.16, 136.53, 168.30, 168.76, 171.11, 211.39, 211.48. MS: 505 (M+1). Anal. ($C_{29}H_{36}N_4O_4$·0.3 $H_2O$) C, H, N.

EXAMPLE 44

Terephthalic acid monomethyl ester

A solution of 20.3 g (100 mmol) terephthaloyl chloride in 100 ml dichloromethane was added to 100 ml anhydrous methanol at 0° C. The reaction was left 1.5 h at rt. The reaction mixture was evaporated and the residue was dissolved dichloromethane. The organic phase was washed with saturated NaHCO$_3$ aq. The organic phase was dried and evaporated. Yield 18.3 g (94.2 mmol, 94%). A solution of 18.3 g (94.2 mmol) of terephthalic acid dimethyl ester and 3.96 g (94.2 mmol) LiOH.H$_2$O in anhydrous methanol (did not dissolve completely) was stirred for 5 d at rt. The solvent was evaporated and the product was dissolved in water. The aqueous phase was washed with dichloromethane. The aqueous phase was made acidic with 2 M HCl aq. The product precipitated from the aqueous phase. The product was filtered off and dried in vacuo. The product was dissolved in 1 L dry ethanol, and thereafter 4 l water was added slowly while stirring. The product precipitated slowly overnight at +4°C. The product was filtered and dried in vacuo. Yield 8.61 g (48 mmol, 51%)

Terephtalic acid mono-(2(S)-benzoylpyrrolidine)amide 1.96 mg (7.1 mmol) BOC-2(S)-benzoylpyrrolidine was deprotected using 14.2 ml trifluoroacetic acid in 70 ml dichloromethane according to procedure J. 1.28 g (7.1 mmol) terephthalic acid mono-methyl ester and the 2(S)-benzoylpyrrolidine trifluoroacetic acid salt were coupled according to procedure. Yield of crude product 1.14 mg. The product was purified with a silica column using 1–2% methanol in dichloromethane as eluent. Yield 540 mg (1.6 mmol, 23%). The methyl ester group of the product was hydrolysed using 101 mg (2.4 mmol) LiOH.H$_2$O according to procedure H. Yield 520 mg (1.6 mmol, 100%).

Terephthalic acid 2(S)-benzoylpyrrolidine L-prolyl-pyrrolidine amide 429 mg (1.6 mmol) BOC-L-prolyl-pyrrolidine was deprotected using 3.2 ml trifluoroacetic acid in 20 ml dichloromethane according to procedure J. 520 mg (1.6 mmol) terephthalic acid mono-2(S)-benzoylpyrrolidine amide and the L-prolyl-pyrrolidine trifluoroacetic acid salt were coupled according to procedure A. Yield of crude product 730 mg. The product was purified with a silica column using 10% methanol in ethyl acetate as eluent. Yield 185 mg (0.39 mmol, 24%)

$^{13}$C-NMR: 24.19, 25.35, 25.55, 26.24, 28.98, 29.48, 46.04, 46.41, 50.06, 50.25, 58.18, 61.43, 127.18, 127.37, 128.57, 128.71, 133.36, 135.31, 137.89, 138.11, 168.65, 168.68, 170.35, 197.48. MS: 474 (M+1). Anal. (C$_{28}$H$_{31}$N$_3$O$_4$.0.6 H$_2$O) C, H, N.

EXAMPLE 45

Isophthalic acid 2(S)-benzoylpyrrolidine L-prolyl-pyrrolidine amide 880 mg (3.2 mmol) BOC-2(S)-benzoylpyrrolidine was deprotected using 6.5 ml trifluoroacetic acid in 30 ml dichloromethane according to procedure J. 1.0 g (3.2 mmol) isophthalic acid mono-L-prolyl-pyrrolidine amide and the 2(S)-benzoylpyrrolidine trifluoroacetic acid salt were coupled according to procedure A. Yield of crude product 1.27 g. The product was purified with a silica column using 10% methanol in ethyl acetate as eluent. Yield 420 mg (0.89 mmol, 28%)

$^{13}$C-NMR: 24.20, 25.39, 25.61, 26.25, 29.00, 29.50, 46.05, 46.43, 50.15, 50.34, 58.28, 61.51, 126.04, 128.11, 128.37, 128.58, 128.69, 129.09, 129.16, 133.30, 135.36, 136.51, 168.55, 168.60, 170.37, 197.41. MS: 474 (M+1). Anal. (C$_{28}$H$_{31}$N$_3$O$_4$.0.7 H$_2$O) C, H, N.

EXAMPLE 46

Isophthalic acid di-(L-alanyl-pyrrolidine)amide 1.21 g (5.0 mmol) BOC-L-alanyl-pyrrolidine was deprotected using 10 ml trifluoroacetic acid in 30 ml dichloromethane according to procedure J. The L-alanyl-pyrrolidine trifluoroacetic acid salt (dichloromethane) was added to 0.51 g (2.5 mmol) isophthaloyl chloride (diethyl ether) according to procedure D. Yield of crude product 1.16 g. The product was purified by a silica column using 10% methanol in ethyl acetate as eluent. Yield 980 mg (2.4 mmol, 95%).

$^{13}$C-NMR: 18.26, 24.16, 26.10, 46.15, 46.51, 47.41, 125.62, 128.80, 130.33, 134.46, 165.74, 171.00. MS: 415 (M+1). Anal. (C$_{22}$H$_{30}$N$_4$O$_4$.0.2 H$_2$O) C, H, N.

EXAMPLE 47

BOC-L-methionine 4.5 g (30 mmol) L-methionine was BOC protected according to procedure E. Yield 6.05 g (24.3 mmol, 81%)

BOC-L-methionyl-pyrrolidine 2.50 g (10 mmol) BOC-methionine was coupled to 1.72 ml (20.6 mmol) pyrrolidine according to procedure B. Yield of crude product 3.38 g. The product was purified with a silica column using ethyl acetate as eluent. Yield 2.81 g (9.3 mmol, 93%).

Isophthalic acid di-(L-methionyl-pyrrolidine)amide 910 mg (3.0 mmol) BOC-L-methionyl-pyrrolidine was deprotected using 6 ml trifluoroacetic acid in 30 ml dichloromethane according to procedure J. The L-methionyl-pyrrolidine trifluoroacetic acid salt (dichloromethane) was added to 306 mg (1.5 mmol) isophthaloyl chloride (diethyl ether) according to procedure D. Yield of crude product 650 mg. The product was purified with a silica plate chromatotron using 5% methanol in ethyl acetate as eluent. Yield 560 mg (1.0 mmol, 70%).

$^{13}$C-NMR: 15.75, 24.21, 26.14, 30.56, 32.11, 46.19, 46.64, 50.67, 125.83, 128.56, 130.27, 133.93, 166.10, 170.25. MS: 535 (M+1). Anal. (C$_{26}$H$_{38}$N$_4$O$_4$S$_2$.0.4 H$_2$O) C, H, N.

EXAMPLE 48

Glutaric acid hexamethyleneimine L-prolyl-pyrrolidine amide 510 mg (1.6 mmol) glutaric acid hexamethyleneimine L-proline amide and 0.14 ml (1.7 mmol) pyrrolidine were coupled according to procedure A. Yield of crude product 490 mg. The product was purified with a silica column using 15% methanol in ethyl acetate as eluent. Yield 340 mg (0.94 mmol, 57%).

$^{13}$C-NMR: 20.41, 24.14, 24.84, 26.23, 26.92, 27.19, 27.67, 28.89, 29.15, 32.31, 33.76, 45.89, 45.90, 46.28, 47.36, 47.88, 57.69, 170.71, 171.39, 172.33. MS: 364 (M+1). Anal. (C$_{20}$H$_{33}$N$_3$O$_3$.0.2 H$_2$O) C, H, N.

EXAMPLE 49

3,3-Dimethyl glutaric acid mono-2(S)-cyclopentanecarbonyl)pyrrolidine amide 1.34 g (5.0 mmol) BOC-2(S)-(cyclopentanecarbonyl)pyrrolidine was deprotected using 10 ml trifluoroacetic acid in 25 ml dichloromethane according to procedure J. The 2(S)-(cyclopentanecarbonyl)pyrrolidine trifluoroacetic acid salt and 2.3 ml (16.5 mmol) triethylamine were dissolved in 50 ml tetrahydrofuran. A solution of 710 mg (5.0 mmol) 3,3-dimethyl glutaric acid anhydride in 20 ml tetrahydrofuran was added at 0° C. The reaction was allowed to proceed overnight. The solvent was evaporated, and the residue was dissolved in water and ethyl acetate. The phases were separated and the ethyl acetate phase was washed with 0.1 M HCl aq. The ethyl acetate phase was dried with anhydrous $Na_2SO_4$ and evaporated. Yield of crude product 1.78 g.

3,3-Dimethyl glutaric acid 2(S)-cyclopentanecarbonyl)pyrrolidine L-proline amide 930 mg (3.0 mmol) 3,3-dimethyl glutaric acid mono-2(S)-(cyclopentanecarbonyl)pyrrolidine amide and 500 mg (3.0 mmol) proline methyl ester HCl salt were coupled according to procedure A. Yield of crude product 1.38 g. The ester group of product was hydrolysed using 189 mg (4.5 mmol) $LiOH.H_2O$ according to procedure H. Yield 1.2 g (3.0 mmol, 100%).

3,3-Dimethyl glutaric acid 2(S)-(cyclopentanecarbonyl)pyrrolidine L-prolyl-2(S)-(acetoxyacetyl)pyrrolidine amide 490 mg (1.8 mmol) BOC-2(S)-(acetoxyacetyl)pyrrolidine was deprotected using 4 ml trifluoroacetic acid in 10 ml dichloromethane according to procedure J. 730 mg (1.8 mmol) 3,3Dimethyl glutaric acid 2(S)-(cyclopentanecazbonyl)pyrrolidine L-proline amide and the 2(S)-(acetoxyacetyl)pyrrolidine trifluoroacetic acid salt were coupled according to procedure A. Yield of crude product 1.05 g. The product was purified with a silica column using 5–10% methanol in ethyl acetate as eluent. Yield 550 mg (0.98 mmol 55%).

3,3-Dimethyl glutaric acid 2(S)-(cyclopentanecarbonyl)pyrrolidine L-prolyl-2(S)-(hydroxyacetyl)pyrrolidine amide 550 mg (0.98 mmol) 3,3-dimethyl glutaric acid 2(S)-(cyclopentanecarbonyl)pyrrolidine L-prolyl-2(S)-(acetoxyacetyl)pyrrolidine amide was hydrolysed according to procedure I. Yield of crude product 420 mg. The product was purified with a silica column using 10% methanol in ethyl acetate as eluent. Yield 315 mg (0.61 nmol, 62%)

$^{13}$C-NMR: 24.86, 24.89, 24.98, 25.33, 25.97, 26.14, 26.16, 28.14, 28.17, 28.33, 28.35, 28.37, 28.39, 28.54, 28.57, 28.76, 28.79, 29.52, 29.57, 34.02, 34.27, 43.79, 43.85, 44.04, 44.07, 46.98, 46.99, 47.97, 48.02, 48.11, 48.97, 48.99, 57.45, 57.47, 61.04, 61.09, 63.88, 63.94, 67.03, 67.06, 170.38, 170.48, 170.82, 170.87, 171.30, 171.35, 209.17, 209.21, 211.55, 211.71. MS: 518 (M+1). Anal. ($C_{29}H_{43}N_3O_6.0.2$ $H_2O$) C, H, N.

EXAMPLE 50

BOC-L-phenylalanine 5.0 g (30 mmol) L-phenylalanine was BOC protected according to procedure E. Yield 8.39 g.

BOC-L-phenylalanyl-pyrrolidine 2.65 g (10 mmol) BOC-L phenylalanine was coupled to 1.48 ml (17.8 mmol) pyrrolidine according to procedure B. Yield of active ester 3.22 g (8.9 mmol, 89%). Yield of crude product 3.33 g. The product was purified with a silica column using 1–2% methanol in dichloromethane as eluent. Yield 1.76 g (5.5 mmol, 55%).

Isophtalic acid di-(L-phenylalanyl-pyrrolidine)amide 955 mg (3.0 mmol) BOC-L-phenylalanyl-pyrrolidine was deprotected using 6.0 ml trifluoroacetic acid in 30 ml dichloromethane according to procedure J. The L-phenylalanyl-pyrrolidine trifluoroacetic acid salt (dichloromethane) was added to 306 mg (1.5 mmol) isophtaloyl chloride (diethyl ether) according to procedure D. Yield of crude product 2.24 g. The product was purified by a silica column using 1–8% methanol in ethyl acetate as eluent. Yield 310 mg (0.55 mmol, 36%).

$^{13}$C-NMR: 24.04, 25.78, 39.55, 45.87, 46.47, 53.09, 125.58, 127.03, 128.46, 128.81, 129.50, 130.54, 134.20, 136.46, 165.89, 169.86. MS: 367 (M+1). Anal. ($C_{22}H_{26}N_4O_3.1.5$ $H_2O$) C, H, N.

EXAMPLE 51

Glutaric acid L-prolyl-L-proline hexamethyleneimine amide 380 mg (1.2 mmol) glutaric acid hexamethyleneimine L-proline amide and 200 mg (1.2 mmol) L-proline methyl ester HCl salt were coupled according to procedure A. The product was purified with a silika column using 10–20% MeOH in EtOAc as eluent. Yield 420 mg (1.00 mmol, 83%). The methyl ester group of the product was hydrolysed using 63 mg (1.5 mmol) $LiOH.H_2O$ according to procedure H. Yield 390 mg (0.96 mmol, 96%).

Glutaric acid L-prolyl-L-prolineamide hexamethyleneimine amide 0.04 ml (0.42 mmol) ethyl chloroformate was added to a solution of 170 mg (0.42 mmol) glutaric acid L-prolyl-L-proline hexanethyleneimine amide and 0.06 ml (0.42 mmol) triethylamine in THF at −10° C. After 20 min 0.14 ml (2.1 mmol) 25% ammonia aq was added and the reaction mixture was stirred overnight at rt. The reaction mixture was evaporated, dissolved in DCM and filtrated. The filtrate was washed with saturated $NaHCO_3$ aq, dried with anhydrous $Na_2SO_4$ and evaporated. Yield 150 mg (0.36 mmol, 88%).

Glutaric acid L-prolyl-2(S)-cyanopyrrolidine hexamethyleneimine amide 0.08 ml (0.56 mmol) trifluoroacetic anhydride was added to a solution of 150 mg (0.37 mmol) glutaric acid L-prolyl-L-prolineamide hexamethyleneimine amide and 0.15 ml (1.11 mmol) triethylamine in THF at 0° C. The reaction mixture was stirred 2 h in rt, evaporated and dissolved in DCM. The organic phase was washed with 30% citric acid aq, dried with anhydrous $Na_2SO_4$ and evaporated. The product was purified with a silica column using 10% MeOH in EtOAc as eluent. Yield 76 mg (0.20 mmol, 53%).

$^{13}$C-NMR: 20.34, 24.95, 25.39, 26.90, 27.16, 27.66, 28.77, 29.12, 29.72, 32.11, 33.69, 45.91, 46.33, 46.51, 47.39, 47.84, 57.44, 118.63, 171.36, 171.73, 172.08. MS: 389 (M+1). Anal. ($C_{21}H_{32}N_4O_3.0.2$ $H_2O$) C, H, N.

EXAMPLE 52

Terephtalic acid mono-pyrrolidine amide 1.08 g (6.0 mmol) terephthalic acid mono-methyl ester and 0.50 ml (6.0 mmol) pyrrolidine were coupled according to procedure A. The product was purified with a silica column using ethyl acetate as eluent. Yield 500 mg (2.1 mmol, 36%). The methyl ester group of the product was hydrolysed using 135 mg (3.2 mmol) LiOH.H₂O according to procedure H. Yield 410 mg (1.9 mmol, 87%).

Terephthalic acid L-proline pyrrolidine amide 410 mg (1.9 mmol) terephthalic acid mono-pyrrolidine amide and 310 mg (1.9 mmol) proline methyl ester HCl salt were coupled according to procedure A. The product was purified with a silica column using 10% methanol in ethyl acetate as eluent. Yield 540 mg (1.6 mmol, 87%). The methyl ester group of the product was hydrolysed using 103 mg (2.5 mmol) LiOH.H₂O according to procedure H. Yield 500 mg (1.6 mmol, 97%).

Terephtalic acid L-prolyl-L-proline pyrrolidine amide 500 mg (1.6 mmol) terephtalic acid L-proline pyrrolidine amide and 270 mg (1.6 mmol) L-proline methyl ester HCl salt were coupled according to procedure A. The product was purified with a silika column using 5–10% MeOH in EtOAc as eluent. Yield 450 mg (1.1 mmol, 67%). The methyl ester group of the product was hydrolysed using 69 mg (1.6 mmol) LiOH.H₂O according to procedure H. Yield 430 mg (1.0 mmol, 99%).

Terephtalic acid L-prolyl-L-prolineamide pyrrolidine amide 0.10 ml (1.0 mmol) ethyl chloroformate was added to a solution of 430 mg (1.0 mmol) terephtalic acid L-prolyl-L-proline pyrrolidine amide and 0.15 ml (1.1 mmol) triethylamine in THF at −10° C. After 20 min 0.071 ml (1.0 mmol) 25% ammonia aq was added and the reaction mixture was stirred overnight at rt. The reaction mixture was evaporated, dissolved in DCM and filtrated. The filtrate was washed with saturated NaHCO₃ aq, dried with anhydrous Na₂SO₄ and evaporated. The product was purified with a silica column using 10–30% methanol in ethyl acetate as eluent. Yield 260 mg (0.63 mmol, 61%).

Terephtalic acid L-prolyl2(S)-cyanopyrrolidine pyrrolidine amide 0.14 ml (1.0 mmol) trifluoroacetic anhydride was added to a solution of 260 mg (0.63 mmol) terephtalic acid L-prolyl-L-prolineamide pyrrolidine amide and 0.27 ml (1.9 mmol) triethylamine in THF at 0° C. The reaction mixture was stirred 2 h in rt. 5 ml water was added and the reaction mixture was evaporated. The residue was dissolved in DCM. The organic phase was washed with 30% citric acid aq, saturated NaCl aq and saturated NaHCO₃ aq., dried with anhydrous Na₂SO₄ and evaporated. The product was purified with a silica column using 30–50% acetonitrile in ethyl acetate as eluent. Yield 145 mg (0.37 mmol, 58%).

$^{13}$C-NMR: 24.44, 25.42, 25.64, 26.38, 28.97, 29.78, 46.22, 46.62, 46.48, 49.49, 50.23, 58.00 118.58, 127.06, 127.28, 137.28, 139.04, 168.85, 168.87, 171.12. MS: 395 (M+1). Anal. ($C_{22}H_{26}N_4O_3$.0.5 $H_2O$) C, H, N.

EXAMPLE 53

3,3-Dimethyl glutaric acid mono-hexamethyleneimine amide 1.0 g (7.0 mmol) glutaric acid anhydride was added to a solution of 1.74 ml (15.4 mmol) hexamethyleneimine in 10 ml tetrahydrofuran. The solution was stirred overnight at rt. The reaction mixture was evaporated, dissolved in an aqueous NaOH solution and washed with dichloromethane. The aqueous phase was acidified with 3 M HCl aq and the product was extracted with dichloromethane. The combined organic phases were dried with anhydrous Na₂SO₄ and evaporated. Yield 1.53 g (6.3 mmol, 90%).

3,3-Dimethyl glutaric acid hexamethyleneimine L-proline amide 500 mg (2.1 mmol) 3,3-dimethyl glutaric acid mono-hexamethyleneimine amide and 340 mg (2.1 mmol) L-proline methyl ester HCl salt were coupled according to procedure A The product was purified with a silica column using 25–50% ethyl acetatein petroleum ether as eluent. Yield 550 mg (1.6 mmol, 74%). The methyl ester group of the product was hydrolysed using 100 mg (2.4 mmol) LiOH.H₂O according to procedure H. Yield 520 g (1.5 mmol, 99%).

3,3-Dimethyl glutaric acid hexamethyleneimine L-prolyl-L-proline amide 520 mg (1.5 mmol) 3,3-dimethyl glutaric acid hexamethyleneimine L-proline amide and 260 mg (1.5 mmol) L-proline methyl ester HCl salt were coupled according to procedure A. The product was purified with a silica column using 10% MEOH in EtOAc as eluent. Yield 540 mg (1.2 mmol, 78%). The methyl ester group of the product was hydrolysed using 76 mg (1.8 mmol) LiOH.H₂O according to procedure H. Yield 520 mg (1.2 mmol, 99%).

3,3-Dimethyl glutaric acid hexamethyleneimine L-prolyl-L-prolineamide amide 0.12 ml (1.3 mmol) ethyl chloroformate was added to a solution of 540 mg (1.2 mmol) 3,3-Dimethyl Glutaric Acid Hexamethyleneimine L-prolyl-L-proline Amide and 0.17 ml (1.2 mmol) triethylamine in THF at −10° C. After 20 min 0.084 ml (1.2 mmol) 25% ammonia aq was added and the reaction mixture was stirred overnight at rt. The reaction mixture was evaporated, dissolved in DCM and filtrated. The filtrate was washed with saturated NaHCO₃ aq, dried with anhydrous Na₂SO₄ and evaporated. Yield 450 mg (1.04 mmol, 84%).

3,3-Dimethyl glutaric acid hexamethyleneimine L-prolyl-2 (S)-cyanopyrrolidine amide 0.22 ml (1.6 mmol) trifluoroacetic anhydride was added to a solution of 450 mg (1.04 mmol) 3,3-dimethyl glutaric acid hexamethyleneimine L-prolyl-L-prolineamide amide and 0.43 ml (3.1 mmol) triethylamine in THF at 0° C. The reaction mixture was stirred 6 h in rt. 5 ml water was added and the reaction mixture was evaporated. The residue was dissolved in DCM. The organic phase was washed with 30% citric acid aq, saturated NaCl aq and saturated NaHCO₃ aq, dried with anhydrous Na₂SO₄ and evaporated. The product was purified with a silica column using 30–50% acetonitrile in ethyl acetate as eluent. Yield 250 mg (0.60 mmol, 58%).

$^{13}$C-NMR: 25.01, 25.38, 26.80, 26.99, 27.70, 28.53, 28.64, 28.73, 29.09, 29.69, 33.98, 42.10, 43.80, 45.87, 46.22, 46.51, 48.10, 48.41, 57.42, 118.66, 171.12, 171.37, 171.51. MS: 417 (M+1). Anal. ($C_{23}H_{36}N_4O_3$.0.1 $H_2O$) C, H, N.

Determination of Inhibitory Effect of Novel Compounds on Prolyl Oligopeptidase Activity of Pig Brain The inhibitory effect of the novel compounds on POP activity of pig brain was determined with a method based on that described by Toide et al. (Toide, K, Iwamoto, Y., Fujiwara. T., Abe, H., *J. Pharmacol. Exp. Ther.*, 274, 1370–1378 (1995)) for the rat enzyme.

The whole pig brains, excluding cerebellum and most of the brain stem, of three pigs were placed in liquid nitrogen within 30 min from killing and stored at −80° C. until homogenized. The brains were homogenized with a glass-teflon homogenisator in 3 volumes (w/v) of ice-cold 0.1 M sodium-potassium phosphate buffer (pH 7.0) and the homogenates were centrifuged for 20 min at 4° C. at 10000 g. The supernatants were collected, pooled and stored in small aliquots at −80° C. until used. The supernatant was thawn in ice just before activity assay and diluted in a ratio 1:2 with homogenisation buffer (=enzyme preparation).

In the microplate assay procedure, 10 μl of enzyme preparation was preincubated with 460 μl of 0.1 M sodium-potassium phosphate buffer (pH 7.0) and 5 μl of a solution of novel compound dissolved in DMSO and diluted with 0.1 M sodium-potassium phosphate buffer at 30° C. for 30 min. The controls contained 10 μl enzyme preparation and 465 μl of 0.1 M sodium-potassium phosphate buffer (pH 7.0). The reaction was initiated by adding 25 μl of 4 mM Suc-Gly-Pro-AMC (AMC: 7-amido-4-methylcoumarin) dissolved in 0.1 M sodium-potassium phosphate buffer (pH 7.0), and the mixture was incubated at 30° C. for 60 min. The reaction was terminated by adding 500 μl of 1 M sodium acetate buffer (pH 4.2).

Formation of 7-amido-4-methylcoumarin was determined fluorometrically with microplate fluorescence reader (excitation at 360 nm and emission at 460 nm). The final concentration of novel compounds in the assay mixture varied from $10^{-12}$ M to $10^{-4}$ M.

The prolyl oligopeptidase activity was calculated with the following formula in the presence of various concentrations of novel compounds. To reveal the inhibitory potency of the novel compound, activities (% of control) were plotted against the log concentration of the compound, and the $IC_{50}$ value was determined by non-linear regression utilizing GraphPad Prism software.

Activity (% of control)=a/b×100, where
a=flourescence intensity in the presence of a novel compound
a=flourescence intensity without a novel compound (control)

The novel compounds exhibit high inhibition potency against pig brain prolyl oligopeptidase. The results are summarized in Table 1.

TABLE 1

Inhibition of pig brain prolyl oligopeptidase.

| Compoud of example No. | $IC_{50}$ [nM] |
|---|---|
| 4 | 48 |
| 11 | 26 |
| 12 | 1.5 |
| 18 | 0.8 |
| 21 | 0.8 |
| 22 | 0.4 |
| 39 | 1.3 |
| 41 | 78 |
| 42 | 13 |
| 46 | 87 |
| 47 | 110 |
| 48 | 28 |
| 50 | 79 |

Inhibitory Activity Against Other Proline Specific Proteases

The novel compounds were tested for specificity of inhibitory activity against formation of 7-amino-4-methylcoumarin from specific substrates of other proline specific in the pig brain.

Determination of Inhibitory Effect of Novel Compounds on Dipeptidyl Peptidase II Activity of Pig Brain By following the procedure for determination of inhibitory effect of novel compounds on prolyl oligopeptidase, but initiating the reaction by adding 25 μl of 0.4 mM H-Lys-Ala-AMC dissolved in 0.1 M sodium-potassium phosphate buffer (pH 7.0), and incubating the mixture at 30° C. for 30 min, the formation of 7-amido-4-methylcoumarin was determined. The dipeptidyl peptidase It inhibition was calculated with the following formula in the presence of a novel compound ($10^{-6}$ M).

Percent inhibition (%)=(1−c/d)×100, where
c=fluorescence intensity in the presence of novel compound
d=fluorescence intensity without novel compound (control)

The novel compounds did not exhibit any inhibitory effect against pig brain dipeptidyl peptidase II.

Determination of Inhibitory Effect of Novel Compounds on Dipeptidyl Peptidase IV Activity of Pig Brain By following the procedure for determination of inhibitory effect of novel compounds on prolyl oligopeptidase, but initiating the reaction by adding 25 μl of 2 mM H-Gly-Pro-AMC dissolved in 0.1 M sodium-potassium phosphate buffer (pH 7.0), the formation of 7-amido-4-methylcoumarin was determined. The dipeptidyl peptidase TV inhibition was calculated with the formula described above in the presence of a novel compound ($10^{-6}$ M).

The novel compounds did not exhibit any inhibitory effect against pig brain dipeptidyl peptidase IV.

The invention claimed is:

1. A compound of the formula (I)

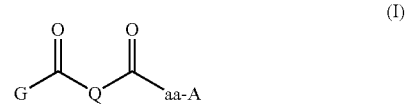

wherein in the formula, the symbol Q is:
a straight or branched alkylene chain having 1 to 6 carbon atoms optionally substituted with 1 to 2 substituent(s) each independently being hydroxy, oxo, lower alkoxy, amino, lower alkyl amino, halogen, carboxyl or lower acyl,
a phenylene group optionally substituted with 1 to 2 substituent(s) each independently being lower alkyl, hydroxy, lower alkoxy, amino, lower alkyl amino, halogen, carboxyl or lower acyl, or
a cycloalkylene group with 5 to 7 carbon atoms optionally substituted with 1 to 2 substituent(s) each independently being lower alkyl, hydroxy, oxo, lower alkoxy, amino, lower alkyl amino, halogen, carboxyl or lower acyl;
the symbol A is:
a straight or branched alkyl chain having 1 to 3 carbon atoms optionally substituted with $COOR^1$, $COR^1$, $COCH_2OR^3$, cyano, hydroxy, oxo, lower alkoxy, amino, lower alkyl amino, or halogen, wherein $R^1$ is H or lower alkyl and $R^3$ is H,
a 5 to 7 membered saturated or unsaturated carbocyclic ring optionally substituted with lower alkyl, $COOR^1$, $COR^1$, $COCH_2OR^3$, cyano, hydroxy, oxo, lower alkoxy, amino, lower alkyl amino, or halogen, wherein $R^1$ is H or lower alkyl and $R^3$ is H, or
a 5 to 7 membered saturated heterocyclic ring optionally substituted with lower alkyl, $COOR^1$, $COR^1$, $COCH_2OR^3$, cyano, hydroxy, oxo, lower alkoxy, amino, lower alkyl amino, or halogen, wherein $R^1$ is H or lower alkyl and $R^3$ is H;
the symbol G is -aa'-E, wherein E is:
a straight or branched alkyl chain having 1 to 5 carbon atoms optionally substituted with $COOR^1$, $COR^1$, COCH₂OR³, cyano, hydroxy, oxo, lower alkoxy, aryloxy, aryl lower alkoxy, amino, lower alkyl amino, aryl amino, aryl lower alkyl amino, or halogen, wherein R¹ is H or lower alkyl and R³ is H, a 5 to 7 membered, saturated or unsaturated, carbocyclic ring optionally substituted with lower alkyl, COOR¹, COR¹, COCH₂OR³, cyano, hydroxy, oxo, lower alkoxy, aryloxy, aryl lower alkoxy, amino, lower alkyl amino, aryl amino, aryl lower alkyl amino, or halogen, wherein R¹ or lower alkyl and R³ is H; or a 5 to 7 membered, saturated or unsaturated, heterocyclic ring optionally substituted with lower alkyl, COOR¹, COR¹, COCH₂OR³, cyano, hydroxy, oxo, lower alkoxy, aryloxy, aryl lower alkoxy, amino, lower alkyl amino, aryl amino, aryl lower alkyl amino, or halogen, wherein R¹ or lower alkyl and R³ is H;

the symbols aa and aa' mean a residue of an α-amino acid, whereby aa can be the same or different from aa', wherein at least one of aa and aa' is L-prolyl, and the other of aa and aa' is L-prolyl, L-alanyl, L-methionyl, L-phenylalanyl, or L-thioprolyl, or a pharmaceutically acceptable salt thereof.

2. The compound according to claim 1, wherein

Q is a straight or branched alkylene chain having 1 to 6 carbon atoms, a phenylene group optionally substituted with lower alkyl, or a cycloalkylene group with 5 to 7 carbon atoms optionally substituted with lower alkyl, A is a straight or branched alkyl chain having 1 to 3 carbon atoms optionally substituted with COOR¹, COR¹, COCH₂OR³, cyano, or halogen, wherein R¹ is H or lower alkyl, and R³ is H, a 5 to 7 membered saturated or unsaturated carbocyclic ring optionally substituted with lower alkyl, COOR¹, COR¹, COCH₂OR³, cyano, or halogen, wherein R¹ is H or lower alkyl and R³ is H, or a 5 to 7 membered saturated heterocyclic ring optionally substituted with lower alkyl, COOR¹, COR¹, COCH₂OR³, cyano, or halogen, wherein R¹ is H or lower alkyl and R³ is H, G is -aa'-E, wherein E is a straight or branched alkyl chain having 1 to 5 carbon atoms optionally substituted with COOR¹, COR¹, COCH²OR³ cyano, hydroxy, amino, or halogen, wherein R¹ is H or lower alkyl and R³ is H, a 5 to 7 membered, saturated or unsaturated, carbocyclic ring optionally substituted with lower alkyl, COOR¹, COR¹, COCH₂OR³, cyano, or halogen, wherein R¹ is H or lower alkyl and R³ is H, a 5 to 7 membered, saturated or unsaturated, heterocyclic ring optionally substituted with lower alkyl, COOR¹, COR¹, COCH₂OR³, cyano, hydroxy, amino, or halogen, wherein R¹ is H or lower alkyl and R³ is H.

3. The compound according to claim 1, wherein

Q is a straight unsubstituted alkylene chain having 2 to 4 carbon atoms, 2,2-dimethylpropylene, or a phenylene group, optionally substituted with 1 to 2 substituent(s) each independently being lower alkyl, hydroxy, lower alkoxy, amino, lower alkyl amino, halogen, carboxyl or lower acyl;

A is a methyl, or a 5 membered saturated carbocyclic ring optionally substituted with lower alkyl, COOR¹, COR¹, COCH₂OR³, cyano, hydroxy, oxo, lower alkoxy, amino, lower alkyl amino, or halogen, wherein R¹ is H or lower alkyl, and R³ is H;

G is -aa'-E, wherein E is a straight or branched alkyl chain having 1 to 15 carbon atoms optionally substituted with COOR¹, COR¹, COCH₂OR³, cyano, hydroxy, oxo, lower alkoxy, aryloxy, aryl lower alkoxy, amino, lower alkyl amino, aryl amino, aryl lower alkyl amino, or halogen, wherein R¹ is H or lower alkyl, and R is H, a 5 to 7 membered, saturated or unsaturated, carbocyclic ring optionally substituted with lower alkyl, COOR¹, COR¹, COCH₂OR³, cyano,hydroxy, oxo, lower alkoxy, aryloxy, aryl lower alkoxy, amino, lower alkyl, amino, aryl amino, aryl lower alkyl amino, or halogen, wherein R¹ or lower alkyl and R³ is H; or a 5 to 7 membered, saturated or unsaturated, heterocyclic ring optionally substituted with lower alkyl, COOR¹, COR¹, COCH₂OR³, cyano,hydroxy, oxo, lower alkoxy, aryloxy, aryl lower alkoxy, amino, lower alkyl, amino, aryl amino, aryl lower alkyl amino, or halogen, wherein R¹ is H or lower alkyl, and R³ is H; and aa is L-prolyl.

4. The compound according to claim 1, wherein Q is a branched or unbranched alkylene with 1 to 6 carbon atoms in the linking chain, or wherein Q is 1,4-phenylene, 1,3-phenylene or 1,2-phenylene.

5. The compound according to claim 1, wherein A is methyl, cyclopentyl, 1-pyrrolidinyl, 2(S)-cyanopyrrolidin-1-yl, 2(S)-(hydroxyacetyl)pyrrolidin-1-yl, 2(S)-formylpyrrolidin-1-yl, 2(S)-(methoxycarbonyl)pyrrolidin-1-yl, 1-azepanyl or 4-morpholinyl.

6. The compound according to claim, wherein E is a branched or unbranched alkyl with 1 to 5 carbon atoms, or wherein E is cyclopentyl, cyclohexyl, cycloheptyl, 1-pyrrolidinyl, 1-piperidinyl, 2(S)-cyanopyrrolidin-1-yl, 2(S)-(methoxycarbonyl)pyrrolidin-1-yl, 4-(tert-butoxycarbonyl)piperazin-1-yl, 1-piperazinyl, 4-morpholinyl, 1-azepanyl, or phenyl.

7. The compound according to claim 1, wherein one of aa and aa' L-prolyl, and the other of aa and aa' is L-alanyl or L-methionyl.

8. The compound according to claim 1, wherein aa and aa' are both L-prolyl.

9. The compound according to claim 1, any wherein Q is a branched or unbranched alkylene with 1 to 6 carbon atoms, or wherein Q is 1,4-phenylene or 1,3-phenylene, A is cyclopentyl, 1-pyrrolidinyl, 2(S)-cyanopyrrolidin-1-yl, 2(S)-(hydroxyacetyl)pyrrolidin-1-yl or 2(S)-formylpyrrolidin-1-yl, E is a branched or unbranched alkyl with 1 to 5 carbon atoms, or cyclopentyl, cyclohexyl, cycloheptyl, 1-pyrrolidinyl, 1-piperidinyl, 1-piperazinyl, 1-azepanyl, or phenyl, and aa and aa' are L-prolyl.

10. The compound according to claim 1, wherein Q is a branched or unbranched alkylene with 1 to 6 carbon atoms, or wherein Q is 1,4-phenylene or 1,3-phenylene, A is cyclopentyl, 1-pyrrolidinyl, 2(S)-cyanopyrrolidin-1-yl, 2(S)-(hydroxyacetyl)pyrrolidin-1-yl or 2(S)-formylpyrrolidin-1-yl, and aa is L-prolyl.

11. A pharmaceutical composition comprising at least one compound as claimed in claim 1 and a pharmaceutically acceptable diluent, carrier and/or excipient.

12. A method for the treatment of Alzheimer's disease or senile dementia, and/or for improving learning and memory functions, which comprises the inhibition prolyl oligopeptidase, whereby a therapeutically effective amount of at least one compound of claim 1 is administered to a subject in need thereof.

* * * * *

UNITED STATES PATENT AND TRADEMARK OFFICE
CERTIFICATE OF CORRECTION

PATENT NO. : 7,173,024 B2  Page 1 of 1
APPLICATION NO. : 10/482700
DATED : February 6, 2007
INVENTOR(S) : Jukka Gynther et al.

It is certified that error appears in the above-identified patent and that said Letters Patent is hereby corrected as shown below:

claim 1, col. 41, line 10, "wherein $R^1$ or lower alkyl" should read -- wherein $R^1$ is H or lower alkyl -- claim 1, col. 41, line 16, "wherein $R^1$ or lower alkyl" should read -- wherein $R^1$ is H or lower alkyl -- claim 2, col. 41, line 52, "cyano, or halogen" should read -- cyano, hydroxy, amino, or halogen -- claim 3, col. 42, line 16, "R' is H" should read -- $R^3$ is H -- claim 3, col. 42, line 20, "lower alkyl, amino" should read -- lower alkyl amino -- claim 3, col. 42, line 22, "wherein $R^1$ or lower alkyl" should read -- wherein $R^1$ is H or lower alkyl -- claim 3, col. 42, line 26, "lower alkyl, amino" should read -- lower alkyl amino -- claim 6, col. 42, line 40, "according to claim, wherein" should read -- according to claim 1, wherein --

Signed and Sealed this

Seventeenth Day of April, 2007

JON W. DUDAS
*Director of the United States Patent and Trademark Office*